US011043142B2

(12) United States Patent
Bova et al.

(10) Patent No.: US 11,043,142 B2
(45) Date of Patent: Jun. 22, 2021

(54) VIRTUAL RADIATION ONCOLOGY CLINIC AND METHODS OF USE THEREOF

(71) Applicant: University of Florida Research Foundation, Inc., Gainesville, FL (US)

(72) Inventors: Frank J. Bova, Gainesville, FL (US); Sanford L. Meeks, Oviedo, FL (US); Twyla R. Willoughby, Orlando, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 15/065,028

(22) Filed: Mar. 9, 2016

(65) Prior Publication Data

US 2017/0053562 A1 Feb. 23, 2017

Related U.S. Application Data

(60) Provisional application No. 62/130,084, filed on Mar. 9, 2015.

(51) Int. Cl.
*G09B 23/28* (2006.01)
*A61N 5/10* (2006.01)
*A61B 34/10* (2016.01)
*G06T 19/20* (2011.01)
*G06T 19/00* (2011.01)

(52) U.S. Cl.
CPC ............. *G09B 23/28* (2013.01); *A61N 5/103* (2013.01); *A61N 5/1037* (2013.01); *A61B 34/10* (2016.02); *G06T 19/003* (2013.01); *G06T 19/20* (2013.01); *G06T 2210/41* (2013.01)

(58) Field of Classification Search
CPC .... A61N 5/103; A61N 5/1037; G06T 19/003; G06T 19/20; G06T 2210/41; A61B 34/10; G09B 23/28
See application file for complete search history.

(56) References Cited

U.S. PATENT DOCUMENTS

| 5,661,773 A | * | 8/1997 | Swerdloff | ............ | A61N 5/1042 |
| | | | | | 378/65 |
| 8,836,697 B2 | * | 9/2014 | Nord | .................... | A61N 5/1031 |
| | | | | | 345/419 |
| 9,764,162 B1 | * | 9/2017 | Willcut | ................... | G06F 19/30 |
| 9,788,783 B2 | * | 10/2017 | Otto | ..................... | A61N 5/1047 |

(Continued)

OTHER PUBLICATIONS

Digital Imaging and Communications in Medicine [Internet]. Rosslyn; [Feb. 5, 2014]. available from: http://medical.nema.org. p. 1.

(Continued)

*Primary Examiner* — Jack Yip
(74) *Attorney, Agent, or Firm* — Thomas Horstemeyer, LLP

(57) ABSTRACT

Methods, systems, and computer instructions for virtual radiation oncology training are provided. The methods can allow for screening of many virtual patients in a clinical setting for radiation oncology training. The methods, system, and computer instructions can include receiving a medical record for a virtual patient, presenting the medical record to a trainee, receiving a treatment plan for the virtual patient from the trainee indicating an area to be treated and dose constraints, and computing one or more comparison metrics for the treatment plan.

20 Claims, 12 Drawing Sheets

(56) References Cited

U.S. PATENT DOCUMENTS

| | | | | |
|---|---|---|---|---|
| 2004/0254773 | A1* | 12/2004 | Zhang | A61B 6/541 703/11 |
| 2005/0111621 | A1* | 5/2005 | Riker | A61N 5/1031 378/65 |
| 2012/0136194 | A1* | 5/2012 | Zhang | A61N 5/103 600/1 |
| 2016/0140300 | A1* | 5/2016 | Purdie | G06F 19/327 705/2 |

OTHER PUBLICATIONS

Spezi E, Lewis DG, Smith CW. A DICOM-RT-based toolbox for the evaluation and verification of radiotherapy plans. Phys Med Biol 2002;47:4223-4232.

Germond JF, Haefliger JM. [Electronic dataflow management in radiotherapy: routine use of the DICOM-RT protocol]. Cancer Radiother 2001;5 Suppl 1:172s-180s.

Huang G, Medlam G, Lee J, et al. Error in the delivery of radiation therapy: results of a quality assurance review. Int J Radiat Oncol Biol Phys 2005;61:1590-1595.

Klein EE, Drzymala RE, Purdy JA, et al. Errors in radiation oncology: a study in pathways and dosimetric impact. J Appl Clin Med Phys 2005;6:81-94.

Fraass BA, Lash KL, Matrone GM, et al. The impact of treatment complexity and computer-control delivery technology on treatment delivery errors. Int J Radiat Oncol Biol Phys 1998;42:651-659.

ASTRO Targeting Cancer Care [Internet]. Fairfax: American Society for Radiation Oncology; [cited Feb. 5, 2014]. available from: http://www.astro.org/. pp. 1-2.

Radiation Therapy Oncology Group [Internet]. Philadelphia: Radiation Therapy Oncology Group; c2104 [cited Feb. 5, 2014]. available from: http://www.rtog.org. p. 1.

Hanna GG, Hounsell AR, O'Sullivan JM. Geometrical analysis of radiotherapy target volume delineation: a systematic review of reported comparison methods. Clin Oncol (R Coll Radiol);22:515-525.

Feuvret L, Noel G, Mazeron JJ, et al. Conformity index: a review. Int J Radiat Oncol Biol Phys 2006;64:333-342.

Allozi R, Li XA, White J, et al. Tools for consensus analysis of experts' contours for radiotherapy structure definitions. Radiother Oncol;97:572-578.

Lyman JT, Wolbarst AB. Optimization of radiation therapy, IV: A dose-volume histogram reduction algorithm. Int J Radiat Oncol Biol Phys 1989;17:433-436.

Lyman JT. Complication probability as assessed from dose-volume histograms. Radiat Res Suppl 1985;8:S13-19.

Okunieff P, Morgan D, Niemierko A, et al. Radiation dose-response of human tumors. Int J Radiat Oncol Biol Phys 1995;32:1227-1237.

Brahme A, Agren AK. Optimal dose distribution for eradication of heterogeneous tumours. Acta Oncol 1987;26:377-385.

Webb S, Nahum AE. A model for calculating tumour control probability in radiotherapy including the effects of inhomogeneous distributions of dose and clonogenic cell density. Phys Med Biol 1993;38:653-666.

Luxton G, Keall PJ, King CR. A new formula for normal tissue complication probability (NTCP) as a function of equivalent uniform dose (EUD). Phys Med Biol 2008;53:23-36.

Seppenwoolde Y, Lebesque JV, de Jaeger K, et al. Comparing different NTCP models that predict the incidence of radiation pneumonitis. Normal tissue complication probability. Int J Radiat Oncol Biol Phys 2003;55:724-735.

Gay HA, Niemierko A. A free program for calculating EUD-based NTCP and TCP in external beam radiotherapy. Phys Med 2007;23:115-125.

Lind BK, Mavroidis P, Hyodynmaa S, et al. Optimization of the dose level for a given treatment plan to maximize the complication-free tumor cure. Acta Oncol 1999;38:787-798.

Cambria R, Jereczek-Fossa BA, Cattani F, et al. Evaluation of late rectal toxicity after conformal radiotherapy for prostate cancer: a comparison between dose-volume constraints and NTCP use. Strahlenther Onkol 2009;185:384-389.

Meeks SL, Buatti JM, Foote KD, et al. Calculation of cranial nerve complication probability for acoustic neuroma radiosurgery. Int J Radiat Oncol Biol Phys 2000;47:597-602.

Rancati T, Fiorino C, Sanguineti G. NTCP modeling of subacute/late laryngeal edema scored by fiberoptic examination. Int J Radiat Oncol Biol Phys 2009;75:915-923.

Rancati T, Wennberg B, Lind P, et al. Early clinical and radiological pulmonary complications following breast cancer radiation therapy: NTCP fit with four different models. Radiother Oncol 2007;82:308-316.

Dunscombe PB, Iftody S, Ploquin N, et al. The Equivalent Uniform Dose as a severity metric for radiation treatment incidents. Radiother Oncol 2007;84:64-66.

Song W, Dunscombe P. EUD-based margin selection in the presence of set-up uncertainties. Med Phys 2004;31:849-859.

Ford EC, Fong de Los Santos L, Pawlicki T, et al. Consensus recommendations for incident learning database structures in radiation oncology. Med Phys;39:7272-7290.

Carlone M, Macpherson M. Detrimental Dose: A Proposed Metric to Score Incidents in Radiation Therapy. Medical Physics 2009;36:1.

Siddon RL. Solution to treatment planning problems using coordinate transformations. Med Phys 1981;8:766-774.

National Comprehensive Cancer Network [Internet]. Fort Washington: National Comprehensive Cancer Network; [cited Feb. 5, 2014]. available from: http://www.nccn.org/default.aspx. p. 1.

Murphy MJ. The importance of computed tomography slice thickness in radiographic patient positioning for radiosurgery. Med Phys 1999;26:171-175.

Langen KM, Willoughby TR, Meeks SL, et al. Observations on real-time prostate gland motion using electromagnetic tracking. Int J Radiat Oncol Biol Phys 2008;71:1084-1090.

Kupelian PA, Lee C, Langen KM, et al. Evaluation of image-guidance strategies in the treatment of localized prostate cancer. Int J Radiat Oncol Biol Phys 2008;70:1151-1157.

Zeidan OA, Langen KM, Meeks SL, et al. Evaluation of image-guidance protocols in the treatment of head and neck cancers. Int J Radiat Oncol Biol Phys 2007;67:670-677.

Huq MS, Fraass BA, Dunscombe PB, et al. A method for evaluating quality assurance needs in radiation therapy. Int J Radiat Oncol Biol Phys 2008;71:S170-173.

Morganti AG, Deodato F, Zizzari S, et al. Complexity index (COMIX) and not type of treatment predicts undetected errors in radiotherapy planning and delivery. Radiother Oncol 2008;89:320-329.

Williams PM. Techniques for root cause analysis. Proc (Bayl Univ Med Cent) 2001;14:154-157.

Voss JD, May NB, Schorling JB, et al. Changing conversations: teaching safety and quality in residency training. Acad Med 2008;83:1080-1087.

Huffman-Dracht HB, McDonnel WM, Guenther E. Resident Education in Medical Errors. The Open Emergency Medicine Journal 2010;3:36-43.

Dror I. A novel approach to minimize error in the medical domain: cognitive neuroscientific insights into training. Med Teach;33:34-38.

Vincent CA. Analysis of clinical incidents: a window on the system not a search for root causes. Qual Saf Health Care 2004;13:242-243.

Vincent C. Understanding and responding to adverse events. N Engl J Med 2003;348:1051-1056.

National Patient Safety Foundation [Internet]. Boston: National Patient Safety Foundation; [cited Feb. 5, 2014]. available from: http://www.npsf.org. p. 1-2.

Farias, et al., Building software agents for training systems: A case study on radiotherapy treatment planning. Knowledge-Based Systems, 10:3, Oct. 1, 1997, pp. 161-168.

Ntasis, et al., Real-Time Collaborative Environment for Radiation Treatment Planning Virtual Simulation, IEEE Transactions on Biomedical Engineering, 49:12, Dec. 2002, 1444-1451.

(56) References Cited

OTHER PUBLICATIONS

American College of Radiology. Reston: American College of Radiology; c2013. p. Radiation Oncology Practice Accreditation Program Requirements; [cited Jan. 2, 2014]. available from http://www.acr.org/~/media/ACR/Document/Accreditation/RO/Requirements.pdf, pp. 1-19.

Cotter GW, Dobelbower RR, Jr. Radiation oncology practice accreditation: the American College of Radiation Oncology, Practice Accreditation Program, guidelines and standards. Crit Rev Oncol Hematol 2005;55:93-102.

Potters L, Gaspar LE, Kavanagh B, et al. American Society for Therapeutic Radiology and Oncology (ASTRO) and American College of Radiology (ACR) practice guidelines for image-guided radiation therapy (IGRT). Int J Radiat Oncol Biol Phys;76:319-325.

Blumber AL, Burns RA, Cagle SW, et al. Safety Is No Accident: A Framework for QUality Radiation Oncology Care. 1 ed: ASTRO; 2012, ii-52.

Kutcher GJ, Coia L, Gillin M, et al. Comprehensive QA for radiation oncology: report of AAPM Radiation Therapy Committee Task Group 40. Med Phys 1994;21:581-618.

Purdy JA, Biggs PJ, Bowers C, et al. Medical accelerator safety considerations: report of AAPM Radiation Therapy Committee Task Group No. 35. Med Phys 1993;20:1261-1275.

Nath R, Biggs PJ, Bova FJ, et al. AAPM code of practice for radiotherapy accelerators: report of AAPM Radiation Therapy Task Group No. 45. Med Phys 1994;21:1093-1121.

Purdy JA, Klein EE, Low DA. Quality Assurance and Safety of New Technologies for Radiation Oncology. Semin Radiat Oncol 1995;5:156-165.

Hartford AC, Palisca MG, Eichler TJ, et al. American Society for Therapeutic Radiology and Oncology (ASTRO) and American College of Radiology (ACR) Practice Guidelines for Intensity-Modulated Radiation Therapy (IMRT). Int J Radiat Oncol Biol Phys 2009;73:9-14.

Fraass BA. Errors in radiotherapy: motivation for development of new radiotherapy quality assurance paradigms. Int J Radiat Oncol Biol Phys 2008;71:S162-165.

Cunningham J, Coffey M, Knoos T, et al. Radiation Oncology Safety Information System (ROSIS)—profiles of participants and the first 1074 incident reports. Radiother Oncol;97:601-607.

Hendee WR. Safety and accountability in healthcare from past to present. Int J Radiat Oncol Biol Phys 2008;71:S157-161.

Nishidai T, Nagata Y, Takahashi M, et al. CT simulator: a new 3-D planning and simulating system for radiotherapy: Part 1. Description of system. Int J Radiat Oncol Biol Phys 1990;18:499-504.

Nagata Y, Nishidai T, Abe M, et al. CT simulator: a new 3-D planning and simulating system for radiotherapy: Part 2. Clinical application. Int J Radiat Oncol Biol Phys 1990;18:505-513.

Aird EG, Conway J. CT simulation for radiotherapy treatment planning. Br J Radiol 2002;75:937-949.

Vertual [Internet]. Hull: Logistics Intitute University of Hull; c2014. [cited Feb. 2, 2014]. available from: http://www.vertual.eu/products/vert, pp. 1-3.

Hamza-Lup FG, Sopin I, Zeidan O. Comprehensive 3D visual simulation for radiation therapy planning. Stud Health Technol Inform 2007;125:164-166.

Seymour NE. VR to OR: a review of the evidence that virtual reality simulation improves operating room performance. World J Surg 2008;32:182-188.

Gordon JA, Vozenilek JA. 2008 Academic Emergency Medicine Consensus Conference. Acad Emerg Med 2008, 971-977.

Kaji AH, Bair A, Okuda Y, et al. Defining systems expertise: effective simulation at the organizational level—implications for patient safety, disaster surge capacity, and facilitating the systems interface. Acad Emerg Med 2008;15:1098-1103.

Issenberg SB, McGaghie WC, Petrusa ER, et al. Features and uses of high-fidelity medical simulations that lead to effective learning: a BEME systematic review. Med Teach 2005;27:10-28.

Mills S, deAraujo, MMT. Learning through virtual reality: a preliminary investigation. Interacting with Computers 1999;11:453-462.

McGaghie WC, Issenberg SB, Petrusa ER, et al. Effect of practice on standardised learning outcomes in simulation-based medical education. Med Educ 2006;40:792-797.

Gondi V, Bernard JR, Jr., Jabbari S, et al. Results of the 2005-2008 Association of Residents in Radiation Oncology Survey of Chief Residents in the United States: Clinical Training and Resident Working Conditions. Int J Radiat Oncol Biol Phys, 1120-1127.

Battles JB. Improving patient safety by instructional systems design. Qual Saf Health Care 2006;15 Suppl 1:i25-29.

Hanley M. Discovering Instructional Design 11: The Kemp Model. vol. 2010; 2010. E-Learning Curve Blog. pp. 1-5.

Anderson JM, Aylor ME, Leonard DT. Instructional design dogma: creating planned learning experiences in simulation. J Crit Care 2008;23:595-602.

Bijhold J, Gilhuijs KG, van Herk M. Automatic verification of radiation field shape using digital portal images. Med Phys 1992;19:1007-1014.

McCullough EC, McCollough KP. Improving agreement between radiation-delineated field edges on simulation and portal films: the edge tolerance test tool. Med Phys 1993;20:375-376.

Yeung D, Palta J, Fontanesi J, et al. Systematic analysis of errors in target localization and treatment delivery in stereotactic radiosurgery (SRS). Int J Radiat Oncol Biol Phys 1994;28:493-498.

Herman MG, Balter JM, Jaffray DA, et al. Clinical use of electronic portal imaging: report of AAPM Radiation Therapy Committee Task Group 58. Med Phys 2001;28:712-737.

Phillips BL, Jiroutek MR, Tracton G, et al. Thresholds for human detection of patient setup errors in digitally reconstructed portal images of prostate fields. Int J Radiat Oncol Biol Phys 2002;54:270-277.

Jaffray DA, Siewerdsen JH, Wong JW, et al. Flat-panel cone-beam computed tomography for image-guided radiation therapy. Int J Radiat Oncol Biol Phys 2002;53:1337-1349.

Jaffray DA. Emergent technologies for 3-dimensional image-guided radiation delivery. Semin Radiat Oncol 2005;15:208-216.

Letourneau D, Wong JW, Oldham M, et al. Cone-beam-CT guided radiation therapy: technical implementation. Radiother Oncol 2005;75:279-286.

Hatherly KE, Smylie JC, Rodger A, et al. A double exposed portal image comparison between electronic portal imaging hard copies and port films in radiation therapy treatment setup confirmation to determine its clinical application in a radiotherapy center. Int J Radiat Oncol Biol Phys 2001;49:191-198.

Mazur LM, Mosaly PR, Jackson M, et al. Quantitative assessment of workload and stressors in clinical radiation oncology. Int J Radiat Oncol Biol Phys;83:e571-576.

U.S. Department of Veterans Affairs [Internet]. Washington DC: U.S. Department of Veterans Affiars; c2014. p. VA National Center for Patient Safety; [cited Feb. 2, 2014]. available from: http://www.patientsafety.va.gov/professionals/onthejob/rca.asp. p. 1-4.

Serrat O. The Five Whys Technique. vol. Feb. 2009. Manila Asian Development Bank; 2009. p. 1-4.

Agency for Healthcare Reseach and Quality Rockville: Agency for Healthcare Reseach and Quality c2008-2014. pp. Plan-do-study-act (PDSA) Cycle [cited 2014 Feb. 2015]. available at: http://www.innovations.ahrq.gov/content.aspx?id=2398. p. 1.

Gould DA, Kessel DO, Healey AE, et al. Simulators in catheter-based interventional radiology: training or computer games? Clin Radiol 2006;61:556-561.

Grone J, Lauscher JC, Buhr HJ, et al. Face, content and construct validity of a new realistic trainer for conventional techniques in digestive surgery. Langenbecks Arch Surg;395:581-588.

Kenney PA, Wszolek MF, Gould JJ, et al. Face, content, and construct validity of dV-trainer, a novel virtual reality simulator for robotic surgery. Urology 2009;73:1288-1292.

Rungtusanatham M. Let's Not Overlook Content Validity. Decision Line Jul. 1998:10-13.

Wynd CA, Schmidt B, Schaefer MA. Two quantitative approaches for estimating content validity. West J Nurs Res 2003;25:508-518.

(56) References Cited

OTHER PUBLICATIONS

Terezakis SA, Harris KM, Ford E, et al. An evaluation of departmental radiation oncology incident reports: anticipating a national reporting system. Int J Radiat Oncol Biol Phys;85:919-923.
Park S, Lee JK, Lee C. Development of a Korean adult male computational phantom for internal dosimetry calculation. Radiat Prot Dosimetry 2006;121:257-264.
Bednarz B, Hancox C, Xu XG. Calculated organ doses from selected prostate treatment plans using Monte Carlo simulations and an anatomically realistic computational phantom. Phys Med Biol 2009;54:5271-5286.
Emami B. Tolerance of normal tissue to therapeutic radiation. Reports of Radiotherapy and Oncology 2013;1(1): 35-48.
Bijhold, J. Three-dimensional verification of patient placement during radiotherapy using portal images, Med. Phys. 20:2 (1993), 347-356.

\* cited by examiner

Overview of Radiation Oncology: Errors (summary of 651 errors in ROSIS)

| 1. Consultation | 2. Planning Preparation | 3. Treatment Planning | 4. Treatment Prep (QA) | 5. Treatment/ Verification |
|---|---|---|---|---|
| •Wrong patient<br>•Incorrect Diagnosis | •Wrong patient<br>•Wrong area scanned<br>•Wrong orientation label (wrong side)<br>•Prescription entered incorrectly (wrong dose/fraction modality)<br>•Prior treatment not accounted for (overdose) | •Wrong area<br>•Computer program not used properly<br>•Bug in computer system<br>•Wrong information used for machine settings<br>•Wrong energy used for planning<br>•General calculation errors<br>•Plan changes | •Chart not checked<br>•Wrong info was put into R&V<br>•Unclear instructions<br>•Data transfer issue<br>•Dose not correctly entered into R&V<br>•Plan changes not checked | •Patient set to wrong location<br>•Machine setup wrong<br>•Wrong beams used<br>•Patient device issues (wrong patient, doesn't fit, used incorrectly)<br>•Machine device issues (broken, used incorrectly, wrong ones used)<br>•Plan changes not implemented<br>•Computer issues (data transfer, machine down) |
| Not included in Radiation Error reporting | 11.8% | 11.6% | 22.0% | 44.6% |

7.8% = Other (overall process issues, special procedures, delays in treatment, etc.)

FIG. 5

| 1. Consultation | 2. Planning Preparation | 3. Treatment Planning | 4. Treatment Prep (QA) | 5. Treatment/ Verification |
|---|---|---|---|---|
| •Multidisciplinary review of patient diagnosis<br><br>•Peer Review - other doctors review appropriateness of treatment | Contours:<br>•Peer review - other doctors review contours<br>•Metrics: Dice's Similarity, volume overlap /under lap between two contours<br><br>Prescription:<br>•Peer Review - other doctors review prescriptions<br>•Compare to published data | Plan Review:<br>•Peer Review - other doctors review plans<br>•Dose volume points (spreadsheet) for each site review specific dose and volume constraints<br>•Summary Metrics : EUD, NTCP, conformity, & coverage compared to "standard" | QA Review:<br>•Plan approved (Y/N)<br>•Fields are approved for treatment (Y/N) | Treatment Delivery:<br>•Verification images to check patient position<br>•Machine parameters and dose tracking<br>•Final plan stats: EUD, NTCP, Conformity and Coverage compared to "standard"<br>•Final treatment review - review overall chart and complete error analysis. |

FIG. 6

VIRTUAL RADIATION ONCOLOGY CLINIC AND METHODS OF USE THEREOF

CLAIM OF PRIORITY

This application claims the benefit of U.S. Ser. No. 62/130,084 filed Mar. 9, 2015, the contents of which is incorporated herein by reference in its entirety.

FIELD OF THE DISCLOSURE

This disclosure is generally in the field of medical training systems, specifically medical training systems in oncology.

BACKGROUND

Residents don't live in the real world. For the most part they exist in training programs that are staffed at much higher levels than the clinics they will join after graduation. They do not develop complex clinical flow scenarios; these have been or will be designed by teaching faculty. They are prevented from making mistakes by exceedingly close supervision. When an error is made the faculty involved is the primary driver of the root cause analysis. A resident's clinical experience is driven by patients as they are randomly presented in clinic, not through a thoughtful process aimed at skill building. To date this is the best that could have been provided in a training program.

Over the past two decades Radiation Oncology has undergone large changes in the imaging, planning and delivery of radiation treatments. What was once a process based on physical exam has been replaced by one that heavily relies upon CT and MR scanning to map disease and normal tissues in 3D. The process for verification of proper plan alignment at the time of radiation treatment, also once based on physically examining a patient on the treatment table, has also been replaced by 2D and 3D electronically produced images. While these technologies have created the ability to deliver more precisely placed, high doses of radiation, they have introduced new avenues for errors to occur that are often more difficult to detect and could have severe consequences. It is known that these errors can occur, yet residents have limited exposure, and therefore limited training opportunities to develop the skill sets allowing them to detect, correct, and most importantly develop systems to prevent such errors. The training in the Radiation Oncology Residency experience has not kept pace with these advances in radiation oncology treatment.

It is therefore an object of this disclosure to provide improved methods and systems for radiation oncology residency experience.

SUMMARY

Systems, programs, and methods for radiation oncology training are provided.

A method of radiation oncology training is provided including (a) receiving a medical record for a virtual patient, (b) presenting the medical record to a trainee, (c) receiving a treatment plan for the virtual patient from the trainee indicating an area to be treated and dose constraints, and (d) computing one or more comparison metrics for the treatment plan. Methods of radiation oncology training are provided wherein the treatment plan comprises one or more contours on a CT dataset in the medical record. Methods of radiation oncology training are provided including (e) generating a simulated treatment record for the virtual patient based upon the treatment plan, (f) presenting the treatment record to the trainee for treatment verification. Methods of radiation oncology training are provided wherein the simulated treatment record includes the treatment and daily dose, and an image file selected from the group consisting of a portal image, a kilovoltage X-ray (KV) image, a computed tomography (CT) image, and a combination thereof. Methods of radiation oncology training are provided wherein the simulated treatment record is simulated to contain one or more patient treatment errors, and wherein the method further includes allowing the trainee to identify if a treatment error has occurred.

Methods of radiation oncology training are provided wherein the treatment errors are selected from the group consisting of a dose error, an error in patient setup during treatment, an error in the treatment time, a technician deviation from the treatment plan, and a combination thereof. Methods of radiation oncology training are provided wherein the treatment metrics include a metric selected from the group consisting of a contour metric, a dosimetry metric, a reporting error metric, and a combination thereof. Methods of radiation oncology training are provided wherein the comparison metrics include a contour metric selected from the group consisting of a conformity index, a similarity coefficient, a volume metric, and combinations thereof. Methods of radiation oncology training are provided wherein the comparison metrics include a dosimetry metric selected from the group consisting of a dose-volume histogram, an equivalent uniform dose, a normal tissue complication probability, a tumor control probability, and a combination thereof. Methods of radiation oncology training are provided wherein the comparison metrics include a reporting error metric selected from the group consisting of a detrimental dose, a severity score, and a combination thereof. Methods of radiation oncology training are provided wherein the comparison metrics include a normal tissue complication probability, an equivalent uniform dose for a target tissue, an equivalent uniform dose for a normal tissue, a tumor control probability for a target tissue, a percentage of target coverage, a conformity index, a detrimental dose, and a severity score.

Systems for radiation oncology training are provided including a medical record module holding medical records of a virtual patient, a treatment simulation module that generates a simulated treatment record for the virtual patient from a treatment plan and the medical records of the virtual patient, and a metrics module that computes one or more comparison metrics from the treatment plan and the treatment record. Systems for radiation oncology training are provided further including a patient management system for viewing and working with the medical records. Systems for radiation oncology training are provided further including a treatment management system for viewing and working with the treatment plan and treatment record. Systems for radiation oncology training are provided, wherein the system generates one or more files in digital imaging and communications in medicine (DICOM) format to be used by the treatment management system. Systems for radiation oncology training are provided, wherein the treatment plan includes one or more contours on a CT dataset in the medical record. Systems for radiation oncology training are provided, wherein the simulated treatment record includes the treatment and daily dose, and an image file selected from the group consisting of a portal image, a kilovoltage X-ray (KV) image, a computed tomography (CT) image, and a combination thereof. Systems for radiation oncology training are provided, wherein the treatment record includes one or more patient treatment errors selected from the group consisting of a dose error, an error in patient setup during treatment, an error in the treatment time, a technician deviation from the treatment plan, and a combination thereof. Systems for radiation oncology training are provided, wherein the comparison metrics include a contour metric selected from the group consisting of a conformity index, a similarity coefficient, a volume metric, and combinations thereof. Systems for radiation oncology training are provided, wherein the comparison metrics include a dosimetry metric selected from the group consisting of a dose-volume histogram, an equivalent uniform dose, a normal tissue complication probability, a tumor control probability, and a combination thereof. Systems for radiation oncology training are provided, wherein the comparison metrics include a reporting error metric selected from the group consisting of a detrimental dose, a severity score, and a combination thereof. Systems for radiation oncology training are provided, wherein the comparison metrics include a normal tissue complication probability, an equivalent uniform dose for a target tissue, an equivalent uniform dose for a normal tissue, a tumor control probability for a target tissue, a percentage of target coverage, a conformity index, a detrimental dose, and a severity score.

Computer readable storage mediums are provided having instructions to cause a computer to: (a) simulate a treatment record for a virtual patient from a treatment plan and a medical record, and (b) compute one or more comparison metrics for the treatment plan. The instructions can include instructions to cause a computer to perform any of the methods described herein. The computer readable storage medium can include instructions to cause the computer to read the treatment record for the virtual patient from an electronic medical records database used in a patient management system. The computer readable storage medium can include instructions to cause the computer to generate the treatment record in a digital imaging and communications in medicine (DICOM) format file to be used by a treatment management system.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 5 is a chart of the common errors of the radiation oncology workflow.

FIG. 6 is a chart of the feedback and metrics of the radiation oncology workflow.

DETAILED DESCRIPTION

Figure 1:
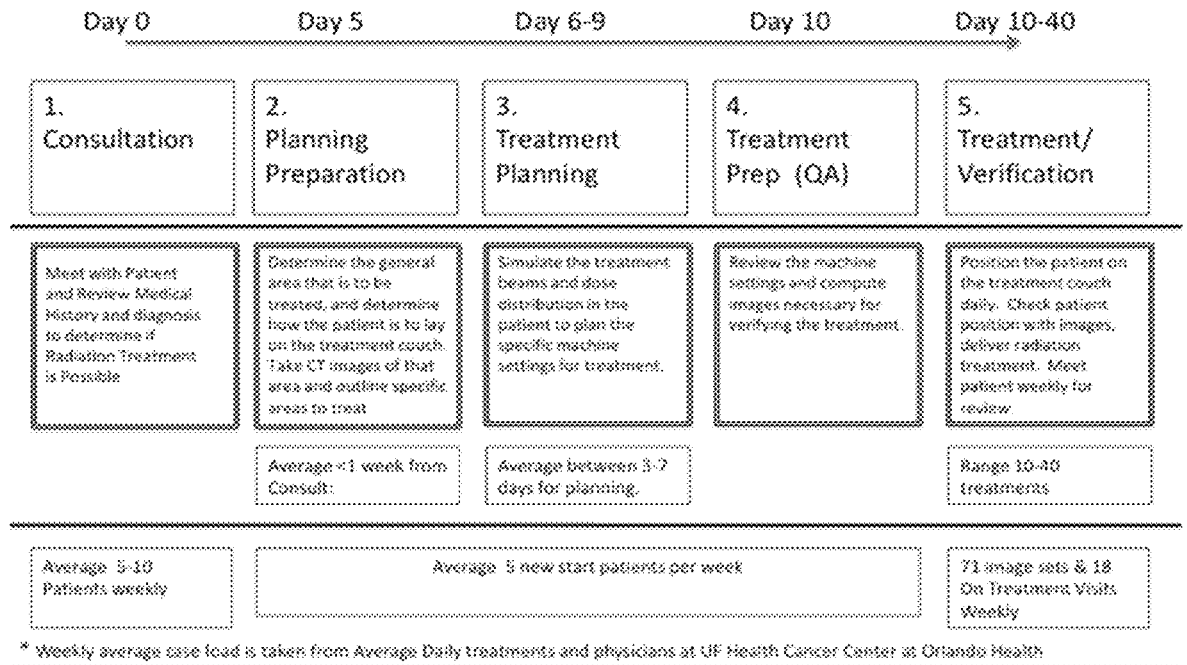
FIG. 1 is a flow diagram of an oncology workflow versus time and workload.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein. Although any methods and materials similar or equivalent to those described herein can also be used in the practice or testing of the present disclosure, the preferred methods and materials are now described. Functions or constructions well-known in the art may not be described in detail for brevity and/or clarity.

Embodiments of the present disclosure will employ, unless otherwise indicated, techniques of molecular biology, microbiology, nanotechnology, organic chemistry, biochemistry, mycology, botany and the like, which are within the skill of the art. Such techniques are explained fully in the literature.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure. In an embodiment, the term "about" can include traditional rounding according to significant figures of the numerical value. In addition, the phrase "about 'x' to 'y'" includes "about 'x' to about 'y'".

Definitions

The terms "subject" or "patient", as used interchangeably herein, refer to both human and non-human or veterinary animals in need of radiation treatment, e.g. for experimental, therapeutic, diagnostic, and/or prophylactic purposes. The term "patient," refers to a subject afflicted with a particular disease, disorder, or condition. Typical subjects and patients include mammals such as mice, rats, rabbits, non-human primates, and humans. When the subject or patient is a human, the human can be an infant (about 0 to 18 months), child (about 1.5 to 12 years), adolescent (about 12-18 years), young adult (about 18 to 35 years), middle adult (about 35 to 55 years), or late adult (over about 55 years).

The terms "virtual subject" and "virtual patent", as used interchangeably herein, refer to a fictitious subject or patient represented by a collection of files on a computer readable storage medium. The virtual patient may be related to an actual subject or patient in that the collection of files may be or may include the medical records of an actual patient. This is not to say that the actual patient and the virtual patient are the same. The files representing the virtual patient may have little or no resemblance to the medical records of an actual patient. The files representing the virtual patient may be derived from the medical records of an actual patient but having personally identifying information removed.

The term "computer readable storage medium", as used herein, refers to any storage medium which can store instructions that are executable by a processor of a computing device. The computer-readable storage medium can be a non-transitory computer-readable storage medium. The computer-readable storage medium can also be a tangible computer readable medium. In some embodiments, a computer readable storage medium can also store data that is able to be accessed by the processor of the computing device. Examples of a computer readable storage medium include, but are not limited to: a floppy disk, a magnetic hard disk drive, a solid state hard disk, flash memory, a USB thumb drive, Random Access Memory (RAM) memory, Read Only Memory (ROM) memory, an optical disk, a magneto-optical disk, and the register file of the processor. Examples of optical disks include Compact Disks (CD) and Digital Versatile Disks (DVD). The term computer readable-storage medium also refers to various types of recording media capable of being accessed by the computer device via a network or communication link. For example data may be retrieved over the internet or over a local area network. The computer readable storage medium can be "computer storage", used herein to refer to any non-volatile computer readable storage medium such as a hard disk drive, a USB thumb drive, a floppy drive, a smart card, a DVD, a CD-ROM, and a solid state hard drive.

The term "computing device", as used herein, refers to any device capable of executing a program or machine executable instructions. References to the computing device comprising "a processor" should be interpreted as possibly containing more than one processor. The term 'computing device' should also be interpreted to possibly refer to a collection or network of computing devices each comprising a processor. Many programs have their instructions performed by multiple processors that may be within the same computing device or which may be even distributed across multiple computing devices. The term 'computer system' may be interpreted herein as being a 'computing device.'

The term "database", as used herein, refers to a collection of logically-related data or files containing data for at least one use or function. Databases are essentially organized data that may be provided or used by an application. Examples of a database include, but are not limited to: a relational database, a file containing data, a folder containing individual data files, and a collection of computer files containing data.

The term "magnetic resonance imaging (MRI)," as used herein, refers to a non-invasive imaging technique which detects atomic resonance from one or more atom(s), or small groups of atoms, having particular proton resonance characteristics when excited by electromagnetic energy at a resonance frequency of the atom, in the presence of one or more magnetic field(s). Resonance is determined at a large number of points throughout the target tissue and assembled by detection instrument(s) into a two- or three-dimensional image map depicting the characteristics of the target tissues.

The terms "MRI" or "MR scanner" are used interchangeably to refer to a MRI system and includes the magnet, the operating components, e.g., RF amplifier, gradient amplifiers and processors that direct the pulse sequences and select the scan planes. Embodiments of the present invention can be utilized with any MRI Scanner including, but not limited to, GE Healthcare: Signa 1.5 T/3.0 T; Philips Medical Systems: Achieva 1.5 T/3.0 T; Integra 1.5 T.

The term "MRI data," is used herein to mean the recorded measurements of radio frequency signals emitted by atomic spins by the antenna of a Magnetic resonance apparatus during a magnetic resonance imaging scan. Likewise, the term "MRI image", as used herein, refers to the reconstructed two or three dimensional visualization of anatomic data contained within the magnetic resonance imaging data. This visualization can be performed using a computer.

ABBREVIATIONS

The following abbreviations are used throughout the present disclosure and, unless otherwise indicated, have the meaning indicated below.
  3DRT 3D radiation therapy
  5 Why's The 5 Why's is a technique used to conduct a root cause analysis of an error or problem and is conducted by asking "why did it happen" five times in series to determine the root cause of the error.

Figure 2:
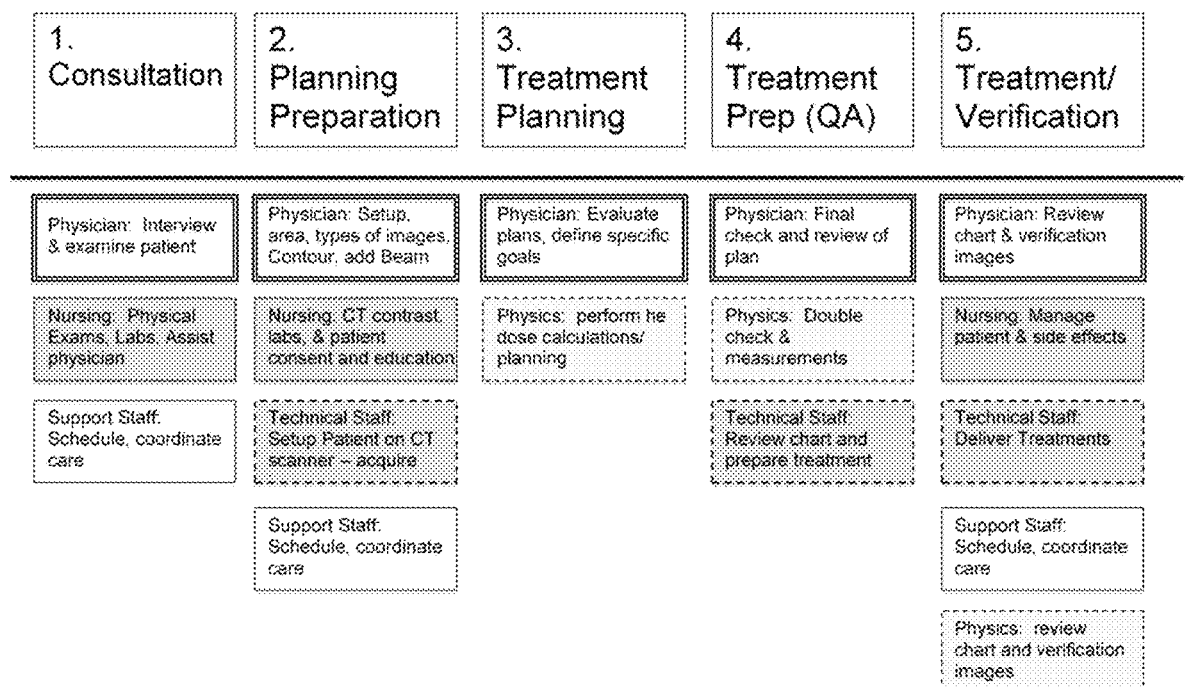
FIG. 2 is a flow diagram of the team member responsibilities in a radiation oncology workflow.
Figure 3:
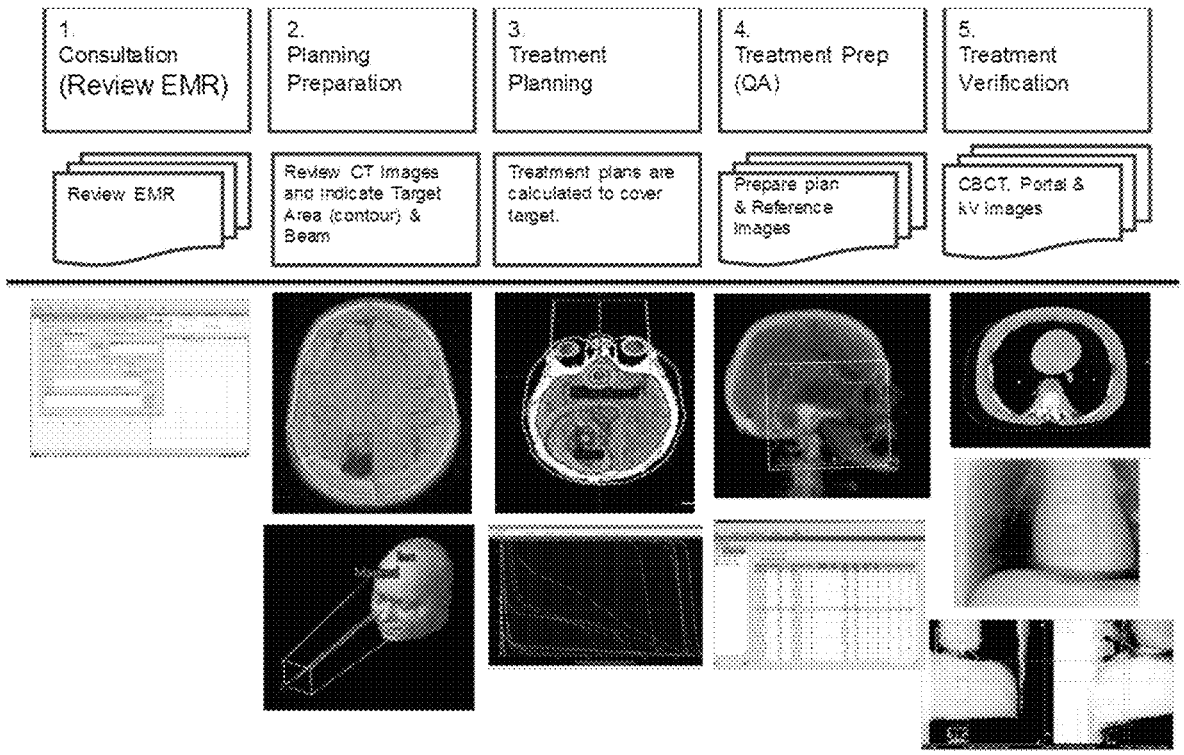
FIG. 3 is a flow diagram of an overview of the radiation oncology workflow.
Figure 4:
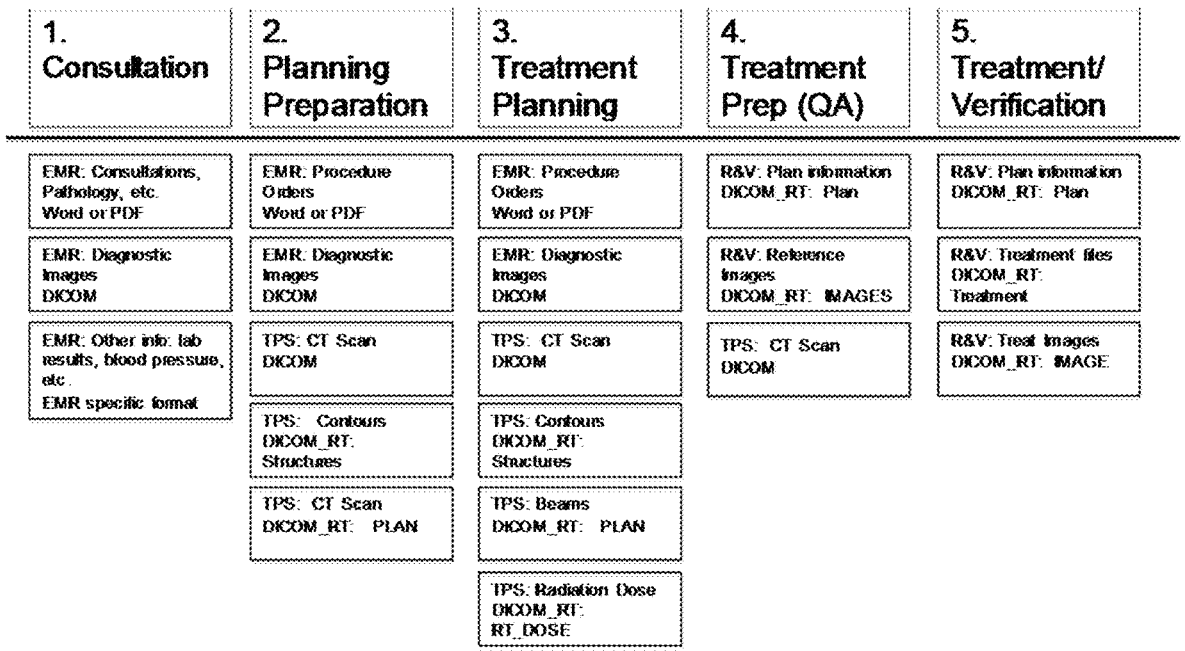
FIG. 4 is a chart of the data elements of the radiation oncology workflow.
Figure 7:
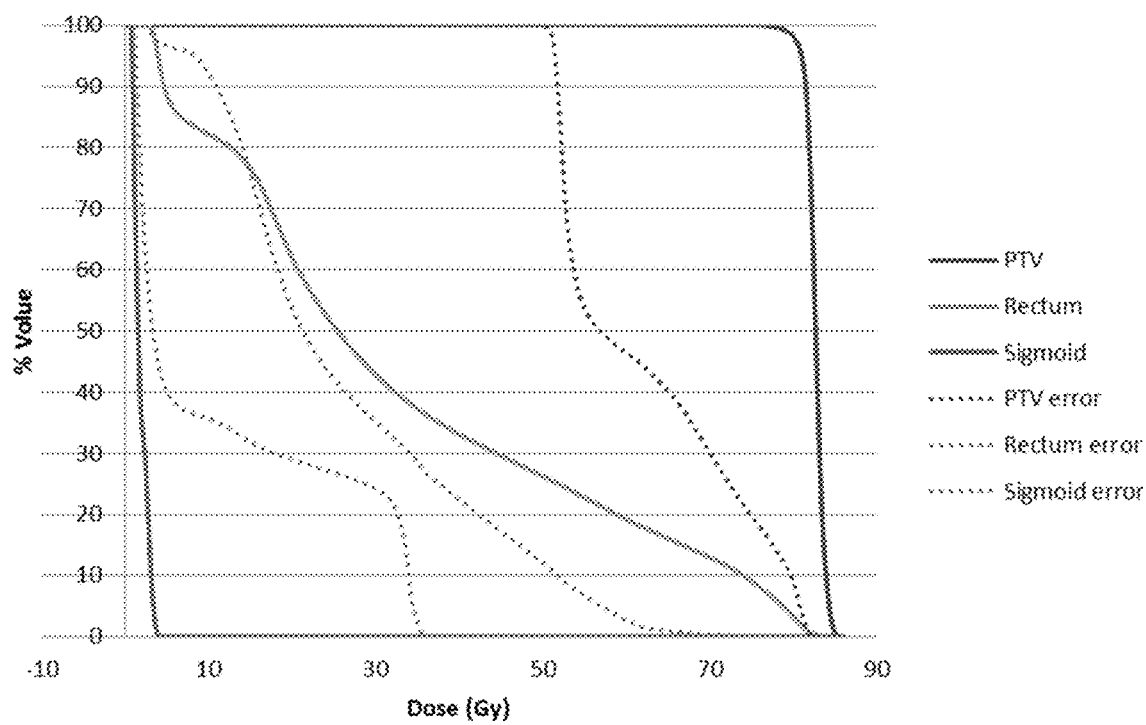
FIG. 7 is an exemplary graph of a sample dose-volume histogram.

AAPM The American Association of Physicists in Medicine
ABR American Board of Radiology
ACGME Accreditation Council for the Graduate Medical Education
ACR American College of Radiology
AHRQ Agency for Healthcare Research and Quality
ARRO Association of Residents in Radiation Oncology
ASTRO American Society of Therapeutic Radiological
ATP Acceptance Test Procedure
CME Continuing Medical Education: Required educational hours for many medical licensures.
CT Computed Tomography This is a methodology for 3D x-ray imaging
DD Detrimental Dose. Calculated by summing the weighted dose change per structure for dose errors
DICOM Digital Imaging and Communication in Medicine—A standard for medical imaging files that allows them to be transferred from one system to another.
Dosimetrist A professional within the radiation oncology department who is specifically trained in the planning and calculating of radiation oncology treatment plans
DRR Digitally Reconstructed Radiograph an x-ray that is reconstructed from a CT scan
DVH Dose Volume Histogram
EMR Electronic medical record. This is a computer system and database specifically for medical purposes. It contains specific medical data.
EUD Equivalent Uniform Dose
Gray (Gy) Dose unit for radiation energy deposited
IGRT Image Guided radiation therapy: The use of daily localization imaging to guide the radiation treatment.
IMRT Intensity modulated radiation therapy
JCAHO Joint Commission on Accreditation of Health Care Organization Currently uses the name The Joint Commission
Linac Linear Accelerator is a method of accelerating partials that can be used as a technique for creating therapeutic radiation
MLC Multi-leaf Collimator—device to shape the radiation beam from the machine.
MOC Maintenance of Certification
MU Monitor Unit: this is a unit of radiation treatment machine time and is related to the dose delivered.
NCI National Cancer Institute
NCPS National Center for Patient Safety
NIH National Institute of Health
NPSF National Patient Safety Foundation
NTCP Normal Tissue Complication Probability
NTCPtot A combined NTCP that was calculated for the purposes of this study-calculated as the product of 1-NTCP for each structure or $(1-\pi(1-NTCP(n))$ for all structures
OAR Organ at risk: Used in treatment planning to describe the non-target tissues
OBI On Board Imaging: This is the name Varian Medical Systems uses to describe the attached kV imaging system on their high energy linear accelerator treatment machines.
PQI Practice Quality Improvements
PRO Practical Radiation Oncology: A journal published by Elsevier specifically addressing clinical issues within radiation oncology
R&V Record and Verify system. A computer system used within radiation oncology to specifically identify the specific details of the radiation treatment. The system interfaces with the treatment machine to capture machine settings to verify the machine settings.
RCA Root Cause Analysis
RO Radiation Oncology
RO-ILS Radiation Oncology-Incident Learning System
TCP Tumor Control Probability
TJC The Joint Commission: organization that accredits hospitals for Medicare reimbursement. Previously called JCAHO
TPS Treatment planning system: A computer system used to develop radiation treatment plans on a patient by patient basis.
UbD Understanding by Design—a methodology for instructional design
UID Unique Identity value: This is a specific number that is used within the DICOM file to identify where the image was created.
VR Virtual Reality
VROC Virtual Radiation Oncology Clinic: Developed specifically for this project, this is a novel simulator that simulates the radiation oncology workflow for physician trainees or resident
Virtual Radiation Oncology Clinic A virtual radiation oncology clinic (VROC) is provided, e.g. for training a radiation oncology resident "trainee". The VROC can take into account the typical workflow in radiation oncology, for example as depicted in FIG. 1. The virtual radiation oncology clinic includes methods of radiation oncology training, systems for radiation oncology instruction, and computer readable storage mediums containing instructions to cause a computer to perform various steps in the methods of radiation oncology training provided herein. The methods, systems, and computer readable storage mediums containing the machine instructions are provided separately in various embodiments. It should be understood that, in other embodiments, the methods, systems, and computer readable storage medium may be provided together in whole or in part as a virtual radiation oncology clinic. The VROC can be designed to focus on the trainee or physician responsibilities, for example simulating the responsibilities of the other team members. A typical delineation of responsibilities can be seen in FIG. 2.

Methods of radiation oncology training are provided. In particular, virtual methods of radiation oncology training are provided. The virtual radiation oncology training methods can include methods of preparation, planning, prescribing, simulating, or monitoring radiation oncology treatment of a virtual patient, or any combination thereof.

The methods can include receiving a medical record for a virtual patient, and/or presenting a medical record for a virtual patient to a trainee. In some embodiments a system is provided with a medical record module containing the medical records of a virtual patient. It can also contain a patient management system for viewing and working with the medical records. The medical records can be in a database of medical records that can include medical records of many virtual patients. The virtual radiation oncology clinic can include a computer readable storage medium containing instructions to cause a computer to read the medical records for the virtual patient from the database. In some embodiments the database is part of a larger database of medical records additionally including the medical records of actual patients. For example, the medical records of the virtual patients may be part of a database for a patient management system used by the physician in the management of actual patients in the hospital environment. In this way, the virtual radiation oncology clinic can be used with a variety of commercially available patient management systems. Furthermore, the trainee can gain experience in the virtual radiation oncology clinic using the same patient management systems used in the hospital setting. The trainee can review the medical record as a virtual consultation, deciding, for instance, if the record warrants radiation treatment.

The trainee can also review CT images of the target area to prescribe a treatment plan for the virtual patient. The methods can include receiving the treatment plan for the virtual patient from the trainee. In some embodiments the treatment plan can be generated by the trainee, while in other embodiments the trainee can be presented with treatment plans. The receiving can include receiving a treatment plan generated by the trainee and/or receiving the treatment plan selected by the trainee from those presented. The treatment plan can indicate, for example, the area to be treated and dose constraints on the treatment. The treatment plan can include dose calculations, directions from which to aim the radiation, the shape of each beam, and/or machine parameters for delivering the radiation. The treatment plan can include one or more contours on a CT dataset in the medical record. The virtual radiation oncology clinic can include a treatment planning module to receive the treatment plan from the trainee. The treatment plan can be entered and/or viewed by the trainee in a treatment planning system. The treatment planning system can contain tools for annotating on the CT images. These tools allow the trainee to "draw" or contour the specific target area if needed, a process referred to as contouring. The TPS can also include computerized graphical models of the radiation treatment machine, or medical linear accelerator. The treatment planning system can be a part of or in addition to the patient management system. In some embodiments, the virtual radiation oncology clinic allows the trainee to use the same treatment planning system used in the hospital setting. For example, in some embodiments the treatment planning system and or module can read and write files in digital imaging and communications in medicine (DICOM) format. The virtual radiation oncology clinic can include a computer readable storage medium containing instructions to cause a computer to read and write treatment plan files in DICOM format.

The virtual radiation oncology clinic can include generating a simulated treatment record for the virtual patient based upon the treatment plan. The simulated treatment record can include any of the standard files generated during radiation oncology treatment. For example, the simulated treatment record can include the treatment given, the daily dose, image file from a portal image, image files from a kilovoltage X-ray (KV) image, images from a computed tomography (CT) image, or a combination thereof. In some embodiments, the virtual radiation oncology clinic includes a treatment simulation module that generates the simulated treatment record. The virtual radiation oncology clinic can include a computer readable storage medium containing instructions to cause a computer to simulate the treatment record from the treatment plan and medical record, and optionally to read and write the simulated treatment record, for example in a DICOM file format that can be read by a treatment management system. The treatment record can be presented to the trainee for treatment verification. In some embodiments the simulated treatment record is simulated to contain one or more patient treatment errors. For example, the virtual radiation oncology clinic can allow the trainee to identify if a treatment error has occurred. Common treatment errors can include a dose error, an error in patient setup during treatment, an error in the treatment time, a technician deviation from the treatment plan, or a combination thereof.

The virtual radiation oncology clinic can include computing one or more comparison metrics. For example, comparison metrics can be computed for the treatment plan or from the simulated treatment record. The comparison metric can be, for example a contour metric, a dosimetry metric, a reporting error metric, or a combination thereof. The system can include a metric module that computes the one or more comparison metrics from the treatment plan and/or the treatment record. The system can include a computer readable storage medium containing instructions to cause a computer to compute the comparison metrics for the treatment plan or simulated treatment record.

The contour metric can include a conformity index, a similarity coefficient, a volume metric, or a combination thereof. Contour metrics can be calculated by comparing the trainee contours to those from an expert on the same CT images. The system can include instructions to cause a computer to convert the contours into 3D polygons and mathematical relationships can be used to calculate the overlap and/or the volume of the polygons. These can be used to compute a similarity coefficient describing the similarity of the two contours, for example, to compute the Dice's similarity coefficient using the equation.

$$D(X, Y) = \frac{2|X \cap Y|}{|X| + |Y|}$$

The contour metric can include a conformity index, for example the Jaccard conformity index.

The dosimetry metric refers to measures of how much energy of radiation will be given as the beam passes through the patient either in total or relative to a reference. As different beams are aimed at the target, this energy will sum up to give a greater dose at their intersection. A dose distribution refers to the results of calculations that indicate how much of the dose is deposited and where. The dosimetry index can include a dose-volume histogram, an equivalent uniform dose, a normal tissue complication probability, a tumor control probability, or a combination thereof.

The reporting error metrics refer to a range of metrics that attempt to quantify outcome based measures, for example based upon the dosimetric severity or upon actual or predicted consequences. The dosimetric severity can be measured, for instance, using a detrimental dose model describe below. In some embodiments, the reporting error metrics are scored on a 0-10 severity scale.

In some embodiments the comparison metrics include a normal tissue complication probability, an equivalent uniform dose for a target tissue, an equivalent uniform dose for a normal tissue, a tumor control probability for a target tissue, a percentage of target coverage, a conformity index, a detrimental dose, and a severity score.

Radiation Oncology Workflow

Examples

An exemplary virtual radiation oncology clinic was implemented using a combination of custom software elements and commercial software elements to simulate a realistic radiation oncology experience. The first step of the development process was to identify specific requirements for simulations for training physician residents. This was done by reviewing the literature on simulations in radiation oncology, simulation in medicine, requirements for radiation oncology training, and instructional design. A final summary of these recommendations was used to advocate specific requirements.

Commercial electronic medical record, record & verify, and radiotherapy treatment planning systems software that are commonly used in a clinical radiation oncology setting were used to provide the features commonly provided by these commercial platforms (See Table 1). An in-kind loan between Varian Medical Systems (Palo Alto, Calif.), University of Florida (Gainesville, Fla.), and UF Health Cancer Center at Orlando Health (previously under the name MD Anderson Cancer Center—Orlando) was granted to provide clinical computer systems to be used to build the VROC system. The commercial software available through this agreement included one Eclipse™ treatment planning station and two Arian™ workstation (R&V and EMR).

One advantage to the Varian system compared to other systems on the market includes the fact that all components of the system utilize a common database. This means that there is a single patient file that is shared between the EMR, TPS and R&V system, eliminating the need for file transfer in and out of different components within the RO workflow. This further facilitates automation for the simulation. Another advantage is that different software products run on a Microsoft Windows platform that can allow the use of other Microsoft or PC-based software to run on the same platform. The commercial software was integrated with custom software tools and documents (See Table 2) developed for the virtual radiation oncology clinic (VROC).

TABLE 1

Varian Medical Systems commercial software used for VROC simulation

| | Varian Name | Module | Description |
|---|---|---|---|
| Electronic Medical Record (EMR) | Aria ™ | Patient Manager | Review patient demographics, documents, test results and radiation treatment summary. |
| | | Time Planner | Scheduling patient appointments and treatments. Can be sorted by location or staff. |
| Record and Verify System (R&V) | Aria ™ | RT Chart | Record treatment goals and prescriptions. Used to track delivered treatments. |
| | | Offline Review | Review of portal images and verification treatment images. |
| Radiotherapy Treatment Planning System (TPS) | Eclipse ™ | Eclipse ™ | Contouring, treatment plan, prescriptions, and calculations. |

TABLE 2

Software and tools developed to create the VROC simulation

| | Tool | Type | Description |
|---|---|---|---|
| User Manuals | Trainee user manual | Document | Manual for trainee or resident |
| | Instructor user manual | Document | Manual for instructor |
| | Director user manual | Document | Manual for director |
| Define Virtual Patient | Scenario request | Form | Request for a specific scenario |
| | Virtual patient checklist | Document | Checklist to create virtual patient |
| Virtual Treatment Machine | Create_MV.m | MATLAB ™ | Generates simulated portal image |
| | Create kV.m | MATLAB ™ | Generates simulated kV/kV images and registration file Shifts registration & changes |
| | Create_CBCT.m | MATLAB ™ | DICOM header of an existing CBCT image set to be loaded into a virtual patient |
| | Create RT.m | MATLAB ™ | Creates RT_TREATMENT record to representing verified beam delivery |
| Simulation Feedback | Prescription form | Form | Trainee's detailed prescription |
| | Contour_comparison.m | MATLAB ™ | Compares two RT_STRUCTURE files |
| | Metrics.m | MATLAB ™ | Generates EUD, NTCP, CI from DVH files |
| | Final report | Document | A report explaining errors that occurred, and summarizing all reported metrics |
| | RCA reporting form | Form | A step by step form to work through a preliminary RCA on the reported case |
| | Final VROC Evaluation | Form | Survey of experience using VROC |

Table 3 is a list of all of the Varian software applications that were available. The specific utility of each software module is described in the table along with the specific step in the RO workflow for the VROC where the application would be used. Some applications are not needed for the VROC because they are designed to support elements of the radiation oncology or medical oncology process that do not need simulation, such as accounts receivable and chemotherapy scheduling and treatments.

TABLE 3

Varian software modules that were used within the implemented VROC

| Module | Work-flow | Description | VROC |
|---|---|---|---|
| Activity Capture | All | Billing and report writing | Not needed |
| Chart QA | 5 | Weekly physicist check | Not needed |
| Document Approval | 1, 2 & 5 | Approve consult, pathology, lab reports. (also duplicated in Patient Manager) | Not needed |
| Archive | 1 | To manage large databases- Duplicated in Administration | Not needed |
| Patient Manager | 1, 2 & 5 | Demographics, documents, radiation treatment summary. | Documents for review, patient under treatment review |
| Report Manager | 5 | Reports of data within the database can be generated | Statistics about the performance of the resident. |
| Time Planner | All | Scheduling patient appointments and treatments. Can be viewed by location or staff. | Manage resident schedule and work list. |
| RT Chart | 3-5 | Treatment goals, prescriptions track delivered treatments. | Evaluate treatment |
| Image Browser | 1 & 2 | Review all images (diagnostic and treatment planning images - can also be done in TPS). | Not Needed. |
| Offline Review | 5 | For reviewing of portal images, and treatment images | Reviewing treatment images |
| Portal Dosimetry | 4 & 5 | For physics QA of IMRT patients | Not needed |
| Eclipse ™ | 2 & 3 | Contouring, treatment plan, prescriptions, calculations | Physician contouring, & plan comparisons |

A protocol was approved through the Internal Review Board (IRB) at UF Health Cancer Center, Orlando at Orlando Health (under the name M.D. Anderson Cancer Center, Orlando) to allow the use of patient records for education purposes and for the development of a simulation training tool. All data had to have patient identification information removed and the patient data was not meant to be shared other than for educational purposes.

The other materials used included software to develop a metrics calculation code, as well as DICOM editing tools and DICOM image management tools. A student license of MATLAB™ (MathWorks, Natick, Mass., USA) was installed on one of the VROC workstation to allow code to be developed for use within the VROC. A free DICOM viewer was used to easily view both the DICOM header and the images throughout the development process. (Santesoft DICOM Viewer 3D, Santesoft, LTC, Athens, Greece).

Specific methodology for developing the VROC system was to detail the desired simulation workflow. This workflow included identifying all elements of the RO workflow as well as interactions between the instructor and the trainee that were specific to the simulation. The general RO workflow had to be broken down for each specific task that was performed. For each task, both the data elements, as well as appropriate software from the materials list were identified. Areas where computer code or a process had to be developed are labeled as VROC. This included any tasks that are typically performed by other RO team members.

Figure 8:
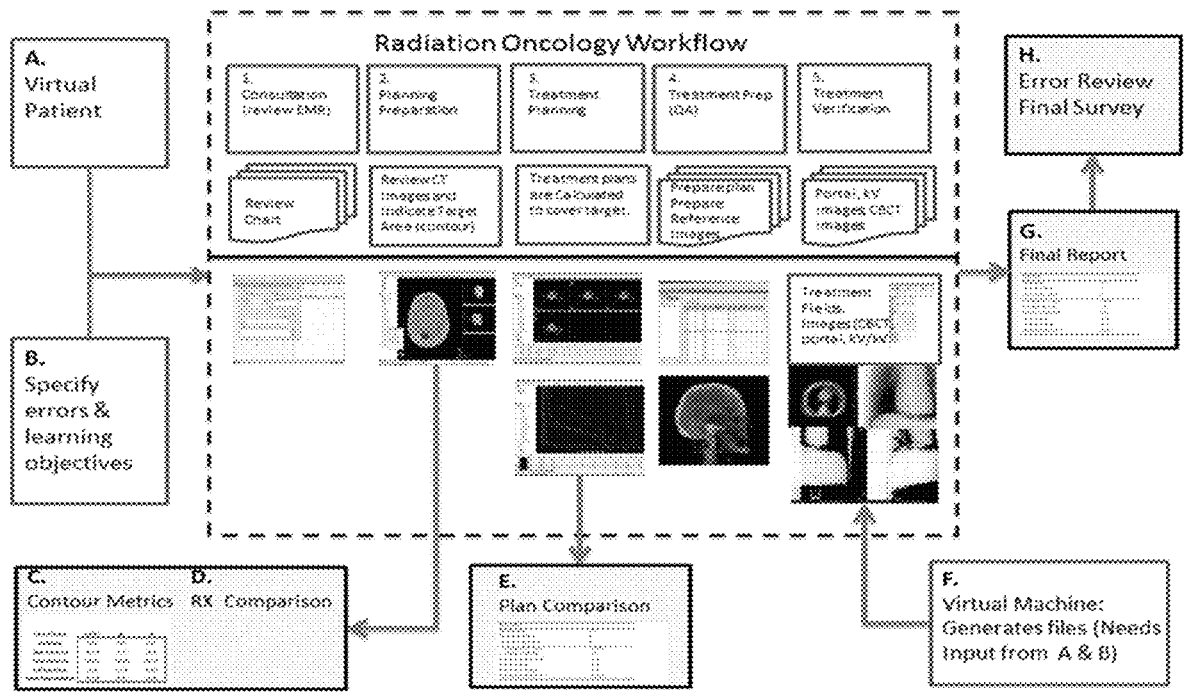
FIG. 8 is flow chart of the virtual radiation oncology clinic development overview.

The aspects of the VROC that were developed can be grouped within eight specific categories that can be identified on a VROC workflow diagram in FIG. 8. The typical RO workflow items are labeled numerically from 1-5. The eight items that were developed are listed below:

A. A virtual patient for RO purposes, and a methodology for creating the virtual patient.

B. A method for describing a specific simulation scenario including patient and simulated error within the VROC system C. A program to calculate contour metrics for contour comparison D. A program or process to check the prescription E. A program to generate a metrics for plan comparison F. A virtual machine to generate the different treatment records and verification images representing daily treatments G. A Program to calculate treatment plan metrics for final treatment review H. A Final feedback and exercise on error mitigation.

Virtual Patient (FIG. 8 A)

The virtual patient represents the collection of all of the data elements needed anywhere within the RO process to simulate a patient receiving radiation therapy. The virtual patient was created by copying and replicating actual patient images and hospital records for a patient who has received radiation therapy. All patient data must be de-identified such that the actual patient identity could not be discovered. It will be part of the simulation director's role to collect these items and organize them for use within the VROC. A detailed procedure and checklist for how to copy, anonymize, and upload these images into the VROC is included in the VROC Director User Manual available at the UF Digital Archive (Object 4-1). Files from real world patients were used to create the virtual patients. Steps 1-5 of the RO workflow are described below to explain how each of the files are used to simulate the patient within the VROC.

Step One of the process was the consultation. For the purposes of the VROC, the face-to-face interaction of the consultation process itself was not simulated. The trainee was, however, able to review all documents and chart information that would typically be available at the time of this consultation within the Patient Manager application. This should be adequate information to determine if radiation is appropriate. The information that was contained in the VROC was taken from an actual real-world patients where all patient identifying information was removed or replaced.

Step Two in the process was the treatment preparation. The information for the virtual patient was created by making a copy of the digital documents and images of an identified real-world patient treatment. The copy of these files was made anonymous, and saved in the virtual patient folder. Files included all required diagnostic imaging as well as the treatment-planning-specific CT and MR images. The actual patient treatment plan, contoured structure files, and dose distributions were retained to compare the simulation values to the expert. This entire patient record was copied, anonymized, and stored in a file called "EXPERT" within the virtual patient file folder so that the structures and the treatment plan could be compared later in the simulation during metric calculations and feedback. Another copy of the entire patient record was created by deleting the treatment plans and dose calculations and deleting the target volume structures. The remaining patient file on the Eclipse™ system included the treatment planning CT, supporting medical images (MRI or PET), and all normal tissue contours. This entire patient record could be copied and stored under the folder "START" within the Virtual Patient file folder so that at any time, the old patient can be purged from this system and a "clean" patient record can be recovered.

Step Three of the process was the treatment planning. This process is not usually performed by the physician; however the physician is skilled in evaluating plans. To simulate a set of treatment plans developed by the physics staff, a set of pre-calculated treatment plans were created when the virtual patient was created. The simulation director was responsible to create the pre-calculated treatment plans based on the initial real-world patient treatment, and based on the type of errors the resident director would like to simulate. The actual patient treatment plan within the TPS was copied and changes were made to create errors within the plans (at the discretion and direction of the instructor). Some of the easiest errors to simulate included changes to prescription and changes to energies. A patient record or file within the Eclipse™ & Arian™ system were able to have many different treatment plans. The simulation training sets typically had between 2-4 different treatment plans. When creating the virtual patient, these plans were created and the entire patient record was archived into a folder named "MULTIPLE" in the virtual patient record.

Specifically within the simulation, once the trainee had completed contours, the director could load the entire patient record from the "MULTIPLE" folder into the virtual patient record that the trainee was working on. This made all of the treatment plans available for review at one time. Once the plans had been uploaded, the trainee was able to review the different plans using tools of the TPS. It was the trainee's responsibility to judge the plans, based on how well they achieve the planning objectives. For treatment plan approval the resident was expected to be able to understand that different screens within the planning system and know how to extract the numbers that were required for them to evaluate a plan. Once the trainee was satisfied that a clinically appropriate plan has been developed, they marked the plan as "approved" within the TPS. Based on the approval of the plan, a set of metrics was generated representing the approved plan compared to the plan that was used to treat the actual real-world patient.

Step Four of the process was plan preparation. Other than approving the treatment plan, the physician did not typically prepare the plan for treatment. This step was the responsibility of the simulation director. Before the treatment plan was ready for treatment, it had to have both "plan approval" in Eclipse™, and "treatment approval" in the RT Chart. These approvals were in part because the system is a clinically available product and these checks are mandated to force a check of all the treatment beams prior to patient treatment. In order for the approved plan to be ready for treatment, each treatment beam in the plan had to have an assigned reference image. The reference images were DRRs that were calculated within the TPS by ray trace through the treatment planning CT scan. The DRRs were reconstructed for each beam angle and represent the ideal patient position for treatment. When the reference images were created, they were assigned a unique DICOM identification number that indicated the specific software used to create the file. Other details included in the DICOM header included all of the details about the beam and patient orientation. The DICOM treatment plan (RT_PLAN) file contained all of the machine settings for each beam for treatment and also included the specific identification number of the reference image assigned to that beam. All of the unique identification numbers (UID) were created when the files were created and approved. When virtual patient treatment occurs, the treatment verification images and treatment files referenced the correct plan UID and image UID in order to match the files to the correct patient, plan, and reference image. Because of these details with the DICOM header and the UID, all files were created in real time as part of the simulation process and were not prepared ahead of time.

Step Five in the process was the treatment delivery and the radiographic verification images that were taken at the time of treatment. Daily treatments were represented in the R&V system by both treatment records of machine settings that are used to chart the number of daily treatments given and the accumulated dose. Verification or localization imaging was checked using R&V software. The files representing daily treatments were uploaded on a day-to-day basis so that the simulation was run in real-time.

When the virtual patient was created, template images representing portal images and kV x-ray images for a perfect patient setup were created. The Eclipse™ software allows the user to change the settings when creating the DRR to vary the contrast by changing the relative weighting of different ranges of CT values for the simulated radiograph. It was possible to create DRRs that look more like conventional MV portal images. This process was only done when the virtual patient was created. The template images were further degraded or shifted to represent errors as part of the daily treatment process, which is described in the section on the virtual treatment machine. In addition to the template portal and kV images, if the instructor wanted to use CBCT images for this virtual patient, a dataset of the actual patients CBCT images were stored in the virtual patient file.

Scenario Request (FIG. 8 B)

The VROC system was created specifically for educational purposes. In order to achieve specific educational objectives, the scenario request form was created to allow the instructor to request a specific patient and specific errors to play out as part of a simulation scenario. Each virtual patient could have several different scenarios that vary in the level of complexity. The VROC was intentionally made flexible to accommodate all types of errors that can occur, both dosimetric and spatial errors. In addition, the virtual patient can be set up to contain more than one error. For each scenario it is important that there be specific learning objectives and expected responses from the user when they encounter an error in the VROC simulation. These objectives can be used at the end of the simulation to ensure that trainee learned the desired information or response.

The Scenario Request Form was used in order to build the virtual patient The information that the simulation director needed in order to gather information to build the virtual patient include: actual patient name and/or medical record number, the specific image sets that are needed, and the specific documents that should be replicated.

The instructor could indicate any specific treatment planning errors that they wanted to show to the trainee and why they had chosen these errors. If there is a specific response they expect from the Trainee, they could indicate that as well. The same was needed for treatment delivery errors.

Contour & Prescription Comparison (FIGS. 8 C & D)

After the trainee had reviewed the documentation and diagnosis of the patient, they could review patient CT images and identify the area to target with radiation. The trainee was able to independently log into the TPS, open the patient file, and delineate the target volumes on the CT dataset. This was a typical expectation for actual real world residents working with patients, so there was no difference for the VROC. It is quite common in a busy center for the normal tissue contours to be defined by the dosimetrist or the physicist, so the initial patient file for the virtual patient within the TPS for the VROC system had all of the normal tissues pre-defined, but did not have contours for any of the target structures. When the trainee was done contouring all of the target structures, they saved the treatment plan.

At this time the trainee would also need to specify all of the dose constraints for the plan. The prescription (Rx) within many of the EMR and R&V systems associated with a treatment plan contained only space for a single target structure name with one total dose and the number of treatments. This was inadequate to define the entire treatment plan. Many facilities use a spreadsheet or simple notes to describe the planning intent for the variety of targets and objects at risk. Another form was created for the trainee to fill in all requested doses and dose limits to normal tissues. This form simply had a list of targets that the trainee can fill in, along with corresponding dose and fractionation. For the organs at risk, the trainee could list a dose limit to a specific volume of tissue or a maximum dose. There was also space to record up to eight objects at risk and their corresponding dose limits. Prescription values that were used to treat the actual patient compared to those entered on the prescription form could be compared within the VROC, and the results e-mailed to the trainee as a table.

Contour comparison metrics were calculated by comparing the DICOM structure file that was saved in the VROC system corresponding to the trainee contours compared to the DICOM_RT structure file that was saved in the "EXPERT" folder when the virtual patient was created. This DICOM file contained coordinates per CT slice for each contoured object. The coordinates could be read into MATLAB™ code and converted to a 3D polygon. Mathematical subroutines within MATLAB™ were used to calculate the interception of different 3D objects. This, along with the volumes of the two structures, was used to calculate the Dice's similarity coefficient based on Equation 3-1. The percentage of the expert's target that was excluded in the trainee contour was also listed, and the volume in cubic centimeters of normal tissue that the trainee included within their target volume is calculated. A table of these values can be exported from MATLAB™ and emailed to the trainee and the instructor to compare the contours. An example of these calculations for a lung target case is shown in Table 4.

TABLE 4

Example results of contour comparison report

| Lung training case | Name of structure | | |
|---|---|---|---|
| | GTV | CTV | PTV |
| Dice similarity | 0.05 | 0.14 | 0.19 |
| Expert volumes (cc) | 3.48 | 37.58 | 90.42 |
| Trainee volumes (cc) | 2.93 | 5.65 | 12.31 |
| % of target missed | 95.76 | 92.13 | 89.28 |
| Normal tissue included (cc) | 2.76 | 2.69 | 2.62 |

Plan Comparisons Metrics (FIG. 8 E)

The next area to be developed included feedback metrics comparing different treatment plans. If the trainee chooses a plan with an error, the simulation is stopped and metrics were calculated comparing the plan with errors to the standard plan. The cumulative DVH corresponding to the standard and the error plan could easily be exported from the Eclipse™ workstation, either during the virtual patient preparation or when the metrics were calculated. The DVH file is a file with percentage dose and percentage volume columns for each different contoured structure. All of the metrics for comparison were calculated from the DVH file. The equations and details about how these values were calculated are given below.

Code was adapted to give feedback for the plan comparison. This code calculated EUD and NTCP for normal tissues and EUD and TCP for target structures. Additional required input for the metrics calculations included total number of fractions and the prescribed total dose. The equations for EUD, TCP, and NTCP require specific input that are different for each structure and relate to the radiation response of different tissue types.

From the DVH, the MATLAB™ code was also used to extract the percentage of the target volume within the prescribed dose. Also, of interest was a measure of the conformity of the prescribed isodose line to the target volume. The most common metric for dose conformity that is reported in the literature was the Jaccard conformity index $$J(A, B) = \frac{|A \cap B|}{|A \cup B|} \quad (4\text{-}1)$$

where A is the volume of the target within the prescribed and the intercept of A and B is the total tissue volume within the prescription isodose line. Both of these values can be extracted from the DVH.

The calculation of all of these metrics for both the error plan as well as the plan without errors presents a significant amount of data that could be confusing to the trainee. In order to try to evaluate all of the metrics and their changes with severity of an error, tests were designed to evaluate the metrics and their changes with severity to recommend a final report for the VROC system. This is discussed below.

Virtual Treatment Machine (FIG. 8 F)

When the resident had selected an acceptable plan for treatment, the patient will proceed with virtual treatment. The intent of the VROC was that it would run in real time so each day represented a single treatment. The virtual treatment machine is a collection of four different computer programs. The file that represents the treatment and daily dose was created. The other three programs correspond to the three different imaging types available: portal Images, orthogonal kV images, and CBCT images. The information from the Instructors scenario request form was used to select the specific imaging for each virtual patient. Each day the files were created and uploaded into the R&V system for all virtual patients undergoing treatment. Details about the four different programs are described below.

Treatment Record:

The RT_TREAT file is a DICOM record generated by the treatment machine. This DICOM file includes patient treatment plan settings (desired beam settings) and also records actual beam settings at the time of treatment. At the time of treatment an RT_PLAN file was sent to the treatment machine and used to program the treatment machine settings. The machine interfaces with the R&V computer to compare the RT_PLAN settings to the actual machine settings. Both actual and planned settings were recorded into the RT_TREAT file. To represent a patient treatment error, the parameters in the DICOM file associated with the specific machine setting were changed using MATLAB™. For example to represent a patient setup in the wrong location, the table parameters were changed. To represent a change in the amount of time the machine was on, the MU settings were changed. Within the clinical situation, if the treating therapist does not use the settings from the plan file (within a narrow range), they must acknowledge this deviation and override the parameters from the plan. A line in the treatment record will record this machine override with a time and date stamp of the treating therapists' electronic signature. For patient treatments, the physician does not scrutinize this RT_TREAT file and only uses it as a means of determining if treatment has or has not been given. Therefore, for the VROC purposes, the RT_TREAT file was primarily used so that the dose accumulation within the VROC was accurate.

Portal Images:

Portal images were described previously. These images are of a poorer quality than traditional kV x-rays. Also, they are taken to represent the actual beam shape for treatment, and therefore are often of a very small cross-section of the patient and show limited anatomy. A template MV portal image was created as part of creating the virtual patient. This template MV image was then modified to create the daily verification portal image for the VROC.

The specific modifications to the image for the VROC included changing the DICOM header as well as changing the image itself. The DICOM header information has to be changed to reflect the correct date and time stamp to represent daily treatment. The DICOM UID in the portal image was edited to match the approved treatment plan so the file would load into the system. Other information in the header included the gantry angle and magnification of the image. These were not changed, but were needed in order to modify the image to represent a setup error.

Figure 10:
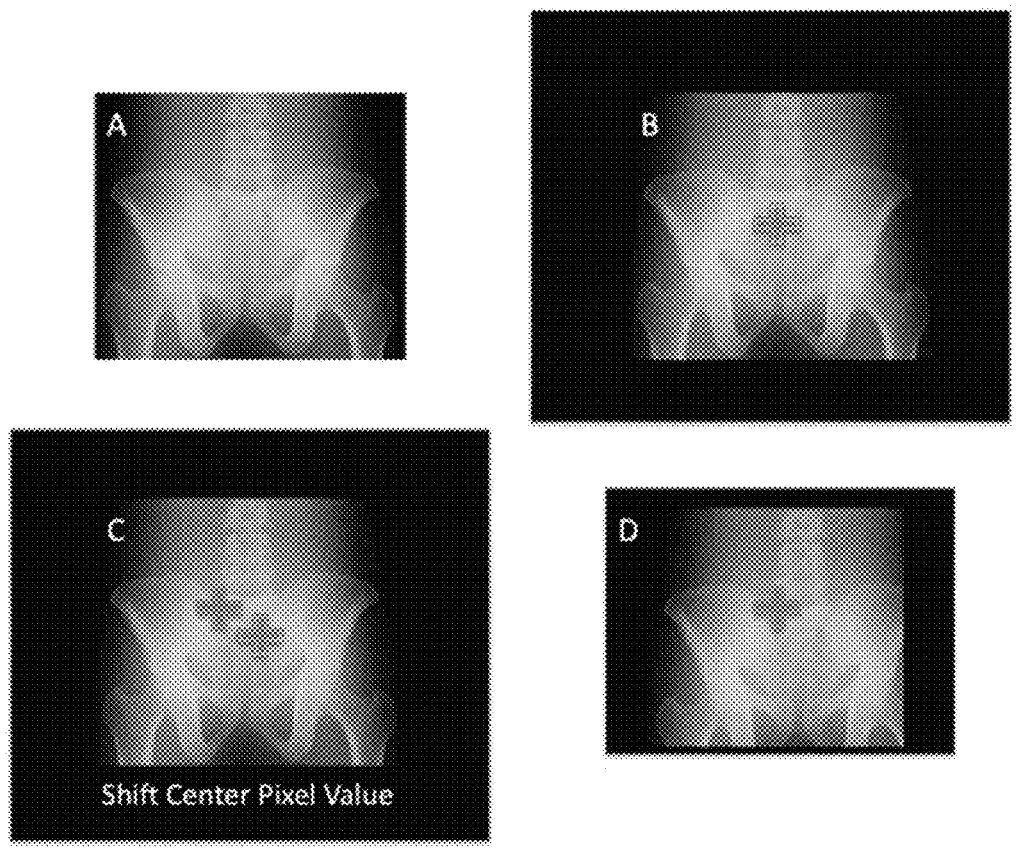
FIG. 10 is a figure demonstrating one method of how setup errors are simulated.

The image could be changed to simulate actual patient setup errors. This was done by shifting the entire image by the amount of the simulated setup error prior to uploading the image into the R&V system. This process is illustrated in FIG. 10. The first panel shows an example x-ray. The center of the image represents the treatment location. Before shifting the image, a set of black pixels is added to the image and the center coordinate is shifted by the amount of the setup error. The center pixel is moved and then an image of the same number of pixels as the original images, but centered on the new location, is written to file. This same process was applied for all image types in order to simulate a setup error.

Another complication for the portal images was that they are taken at a specific gantry angle that may not correspond to the patient Cartesian coordinates used to describe patient setup errors. A matrix transformation was used to convert the patient coordinates to the image coordinates. The transformation used to translate the patient coordinate system to the film coordinate system is given in Equation 4-1 where (u,v,w) are image coordinates, (x,y,z) are patient coordinates, $\theta$ represents the gantry angle, and $\phi$ represents the table angle.

$$\begin{pmatrix} u \\ v \\ w \end{pmatrix} = \begin{pmatrix} x \\ y \\ z \end{pmatrix} \begin{pmatrix} \cos\theta & 0 & \sin\theta \\ \sin\theta & 0 & \cos\theta \\ 0 & 1 & 0 \end{pmatrix} \begin{pmatrix} \cos\varphi & -\sin\varphi & 0 \\ \sin\varphi & \cos\varphi & 0 \\ 0 & 0 & 1 \end{pmatrix} \quad (4\text{-}1)$$

Specific tests were done to test the accuracy of the error simulation.

Daily Kv Image Verification:

Another method of treatment verification required films to be taken daily using a kilovoltage (kV) x-ray source. In this case it is customary to take these kV images as a right lateral (RT) and as an anterior (AP) projection (assuming supine, head first, position). Template kV AP and RT lateral images of the ideal patient position were created when the virtual patient was created. Unlike the single image application of the portal images, the orthogonal image pair allows 3D patient registration within the linac Software. This meant that at the time of patient treatment or images, the machine settings were captured. The 3D registration process was the process of comparing these newly acquired x-ray images to the reference images that were stored in the treatment plan. When the new images indicated that the patient needed to be moved, the treatment couch could be shifted remotely and the new couch positions, along with the magnitude of the shifts, were recorded in a registration File. The registration file also recorded the specific image DICOM Unique Identify Value (UID) for both the new x-ray image and the reference image in the plan.

To simulate setup deviation in the kV images, the template images were loaded into MATLAB™. Code was used to pad the images with black pixels and then to shift the images based on the patient shifts. Code was also used to create a registration file. Depending on the specific situation, the registration file could indicate a correction to the setup error that was introduced in the verification images. Before saving all of the files, the newly simulated kV images and registration file had to reference the UID for the correct treatment plan and for each of the reference images. This was all handled within the subroutines. The final product contained two kV images and a registration file. All three were loaded into the R&V system to represent the image registration process. The testing of this code and the accuracy of different setup error simulations is discussed below.

Treatment Verification CT Images

The final type of image verification used clinically is a 3D dataset of axial slices of Computed Tomography images of the patient. These images are acquired using a Cone-Beam CT technique (CBCT) that uses a single x-ray tube and a flat panel imager. The 3D dataset was reconstructed during acquisition and was used to align the patient based on internal anatomy. The CBCT was also used to detect internal anatomical changes and determine if a plan needs to be modified. The CBCT dataset contained a set of 64 CT slices encompassing approximately 15 cm in length centered on center of the treatment machine rotation (isocenter). The goal was to position the target area of the patient at the isocenter. Due to the imaging equipment, there were couch limitations that do not allow the patient to be set far to the left or the right to make sure the equipment will clear as it rotates around the patient to generate the CBCT. When treating areas far to one side or the other, the images are taken with the patient centered at the machine and after the images are taken the patient is shifted to the treatment location.

The CBCT dataset was a 3D data set so a shift in the patient coordinates corresponded to the same direction in the CBCT coordinate system. Shifts in superior and inferior direction meant that the entire CBCT dataset would load into the review software at a different location relative to the treatment planning dataset. With the current VROC system, this could only be simulated by changing the Z coordinate within the registration file. Shifts in either the lateral direction or in the AP direction could be simulated by physically shifting each of the images the same way, as described in FIG. 10.

Similar to the kV image alignment, a registration file was created at the time the CBCT image was acquired at the actual treatment machine. The registration file contained a list of each of the DICOM UID for both the reference CT scan as well as the CBCT scan in order to match the two image sets together. Because of the complexity of this file, the workflow to generate the CBCT images required the Director to load the trainee-approved treatment plan onto the actual patient treatment machine to create the registration file. This was only done once for each treatment plan. Based on trial and error this was the easiest way to create the record with the correct image UIDs.

Registration File from the 4D Console:

The specific steps that were completed to create the simulated CBCT images are:
 Simulation director exports approved RT plan CT images
 Deliver a CBCT using these files in order to generate a template Registration
 Transfer new Registration file into MATLAB™
 Transfer actual patient CBCT into MATLAB™
 MATLAB™ program to shift images & change header information on real patient CBCT to virtual patient approved plan.
 Save the new CBCT images
 Change the AET of the CBCT images to match a Varian machine
 Change the DICOM tag information for each CBCT image in the Registration file to match the new UID for each DICOM image
 Change the AET of Registration file to Varian machine.
 Final Plan Report (FIG. 8 G)

The final plan report was generated based on the total treatment simulation, and depended on the number of treatments given which contain errors compared to the correct treatments. The simulation director could create a composite treatment plan based on the number of different treatments that were given to the virtual patient. For the initial VROC development, the simulation was stopped early when errors occurred and were undetected. The trainee had two opportunities to correct the error, but if they missed an error after these two attempts, the simulation was stopped. The system assumed that the remaining treatments included the error. The reason the simulation was stopped early was to provide feedback and correction close to the time the error occurs. Because some treatments can go for up to 6 weeks, there was no benefit in allowing a continuation of the error, which could have had the effect of reinforcing the error to the trainee.

If the trainee detected the error, then the error was corrected and the simulation continued. At the end of the simulation, or when the simulation was stopped, the same metrics that were described for the plan comparison were calculated. Ideally, the metrics helped the trainee understand the overall consequences of the error.

Final Error Exercise and Debrief (FIG. 8 H)

It is customary within simulation training to provide an opportunity to answer questions and to give feedback to the trainee at the end of the simulation. This is an opportunity for the instructor and the director to determine if the learning objectives were met. For the VROC, a tool to perform an error mitigation was developed to facilitate some questions for the debrief session between the trainee and the instructor. The error mitigation exercise was created to try to follow specific methods for conducting a root cause analysis (RCA). The exercise itself was a form that forced the trainee to stop and think about the error that occurred and why the error occurred. At the end of each VROC experience, both the Instructor and the Trainee were asked to fill in a survey about the specific simulation to help provide opportunity for improvements in future development and to modify scenarios that are confusing or ones that do not achieve their desired objectives.

Figure 9:
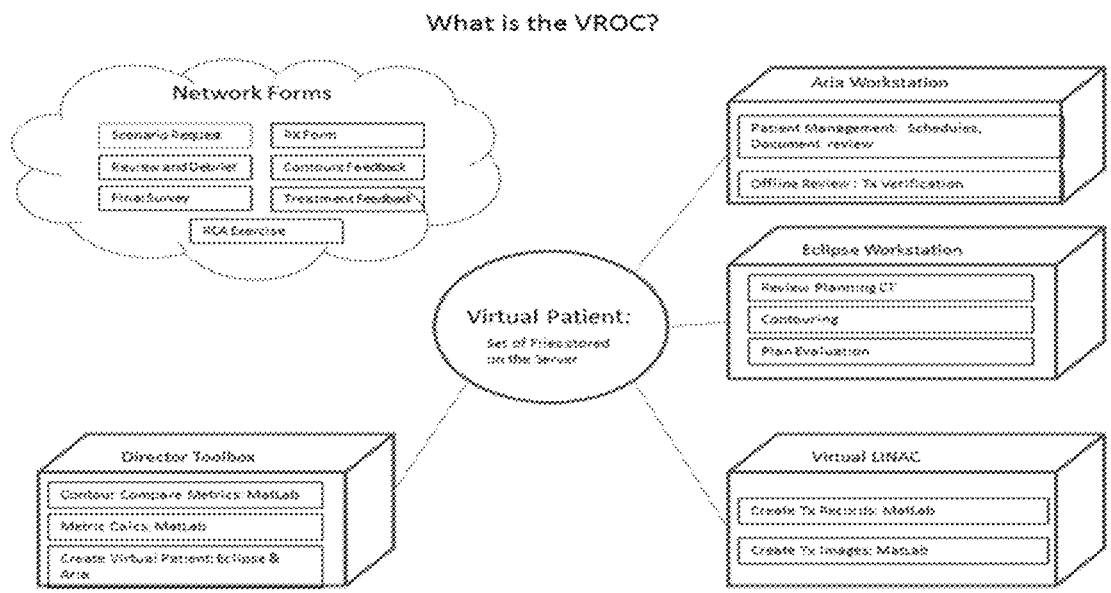
FIG. 9 is a diagram of some components in a virtual radiation oncology clinic.

FIG. 8 was used as part of the development process, to help describe required elements for the VROC and how those elements relate to the overall RO workflow. Once developed, another way to describe the developed items is through a schematic of the VROC system. FIG. 9 is an illustration of the physical layout of the VROC.

Error Simulation Testing

Several different error types were simulated using the VROC system to test the overall VROC process and to test that errors realistically matched actual errors that could occur within a clinical setting. The primary focus was to validate developed software that was created for the VROC system. The components that utilized commercial software were tested to make sure that a particular error could be created, but validation testing was not necessary. In the VROC system, a virtual patient corresponds to a set of DICOM image records that can be loaded into the Varian treatment planning and R&V systems as described previously. In general, radiation errors can be classified as either dosimetric or as spatial. Dosimetric errors are those in which the overall error results primarily in a change in the dose delivered. Spatial errors are those that are primarily a result of the dose being delivered to the wrong location. The dosimetric errors occur most frequently in the preparation and planning steps of the radiation process and spatial errors occur most often at the time of treatment.

Errors in Pre-Planning and Treatment Planning

Within the VROC, contouring error can occur, but for training purposes these errors are not carried through to treatment. Instead, feedback is given to the trainee about the overall agreement of their contour to the expert contour. The instructor can specify how they wish to proceed if the contour does not meet a threshold Dice's similarly coefficient for agreement, such as requiring the trainee to repeat the contour process. Because the contouring tools themselves were commercially available products, there was no need to validate the tools for performing contouring. The validation of the metrics that were calculated relative to the contours is included in the metrics testing discussed below under the heading "Metric Calculations."

Because the VROC system specifically uses commercial software for the developed treatment plans, any type of prescription dose error that can occur in a real clinic can be duplicated within the VROC. In order to simulate a prescription error, the original treatment plan is copied and the prescription dose in the plan is changed. The plan immediately updates with the new information. Several plans with different dose prescriptions were created as part of the testing of the metrics calculations. The added prescription form allows the VROC to simulate a "Peer Review" process by comparing the trainee prescription to the expert prescription. No calculations are done for this review; it is a simple side-by-side comparison per each structure.

Because the VROC system uses a clinical treatment planning station, any clinical treatment planning error can be simulated. It is not typically the physician responsibility to check all of the technical details of plan development, but the physician should check those items that relate to the overall dose distribution by evaluating each CT slice as well as the composite and fractional doses on the DVH. For example the use of the wrong energy should be evident in the treatment plan because the organs of risk may receive too much dose. To simulate this error, the beam energy is simply changed in the treatment plan. Another error could be that the planner failed to account for a specific organ at risk (OAR) a new plan can be generated that overdoses that particular structure. Several different planning errors were simulated as part of the metrics calculations. Specific validation of the accuracy of the dose algorithms within the Varian Eclipse™ system is part of the initial acceptance test process that was completed with Varian when the system was delivered.

Errors in Patient Treatments

Errors in treatment that relate to a dose error can be simulated within the VROC by changing the radiation treatment record. This file is created using code as part of the virtual treatment machine. Within the RO workflow, the only aspects of the daily treatment record that the physician typically evaluates are the number of daily treatments and the accumulated dose. A measure time the machine is on that is related to the dose given is called a monitor unit (MU). The number of the treatment records uploaded will determine the number of treatments. A separate treatment record is created for each beam for each treatment. To simulate an extra treatment a duplicate set of the files can be created and uploaded into the system and it will appear as though all fields were treated twice. To change the dose from any field the MU values can be changed and the dose that is recorded for each beam will change by the same ratio.

Validation was specific to the daily dose tracking. Sets of delivered fields that included under dose from too few MU given as well as from treatment beams not being treated were tested. Over-dose situations where extra fields were treated or the MU was too high were also tested. The set of different dose errors was repeated on three separate patients to make sure that the code to generate the radiation treatment record was correct and that the files could be imported into the RT Chart software and represent the different dose errors.

One of the main quality assurance tools in the daily treatment of patients is through the use of daily or weekly imaging. Within the VROC, errors that occur at the daily treatment are simulated within the verification images by using code that was developed as part of the VROC development. To test the accuracy of the VROC treatment error simulation, a set of tests were developed to test each of the three different image verification methods of the VROC system.

Ground truth for the images and for the error was created using a radiographic phantom to represent a "real world" or physical patient. The VROC process was used to for create a virtual patient by using the CT images of the radiographic phantom as though they represented an actual patient. Prior to scanning the phantom in the CT scanner, a set of metal fiducials were applied on both the anterior and lateral surfaces of the phantom. These were used to remove ambiguity when comparing the image location in the VROC software. For each of the three different verification imaging methods, a "real" patient file was created by scanning the phantom in a CT scanner and placing external marks on the phantom to assist in setting up this "real" patient on the treatment machine.

For each of the three "real" patient files, the phantom was taken to the actual treatment machine (Varian 23ix with OBI) to acquire treatment verification images of the phantom in the correct treatment position as well as a number of other positions representing setup errors. FIG. 5-1 is a photograph of the radiographic phantom on the treatment machine couch. The imaging panels and the kV x-ray source are deployed. The silver reflective markers on the phantom were used as some of the fiducials for the image registration.

The same three "real" patient files were anonymized and their CT data used to create "virtual" patients within the VROC system. Virtual treatment images were created for the virtual patients using the virtual treatment machine code. For validation testing the images and records created by the treatment machine were compared to those simulated in VROC.

All images both real and simulated were imported into the Offline Review (Varian Medical Systems) software that is incorporated into the VROC. The coordinates of the fiducials in each of the images or image pairs were recorded. The differences in these coordinates were compared for all modalities to verify the simulation code for the images accurately simulate setup errors The Offline Review software in VROC handles each of the three imaging modalities differently under normal clinical circumstances. For these reasons, the specifics for each of the three imaging validation tests are handled separately.

Daily Orthogonal kV Images

The treatment plan for the Actual phantom plan was transferred to the treatment machine. The phantom was placed on the treatment couch and aligned to the setup marks that were used for the CT scan that should represent the ideal treatment position. An initial set of orthogonal images was acquired to verify that the phantom was positioned correctly. The treatment machine software was used to compare the x-ray images to the reference images. If the software indicated that the patient should be shifted, this shift of the couch was performed.

1. Four different registration scenarios were identified. And all four possible alignments were checked for three different setup errors in the lateral, longitudinal, and vertical directions (x,y,z) of (3, 2, 1) cm, (2,1,3) cm, (5.4, 4.4, 3.0) cm. The four different registration scenarios are described below.
2. Initially align patient correctly; register images correctly; do not shift patient; Final=patient aligned correctly.
3. Initially align patient correctly; register images incorrectly; shift patient; Final=patient aligned incorrectly.
4. Initially align patient incorrectly; register images correctly—shift patient; Final=patient—aligned correctly.
5. Initially align patient incorrectly; register images incorrectly; do not shift patient; Final=patient aligned incorrectly.

For each set of setup errors and registration situation, the orthogonal images and the registration files were captured at the treatment console. In cases where the registration required the treatment couch to be moved, that translation was physically performed just as it would in an actual patient scenario. In total there were 12 separate sets of image pairs that were taken of the radiographic phantom.

Once all films were acquired they were imported into Offline Review. The coordinates of the fiducials and anatomical landmarks within the image were recorded for each of the images for both the initial phantom position as well as the registered phantom position according to the above 4 different registration scenarios. The known offsets that were introduced were recorded to verify that the coordinates of the fiducials changed by the correct amount.

A virtual patient was created by copying the CT scan for the phantom. The VROC and MATLAB™ code along with the template images were used to virtually recreate each of the different setup errors and alignment scenarios create. A set of 12 separate image pairs was created for the virtual patient. The simulated kV alignment films were loaded into the corresponding virtual patient in Offline Review. The coordinates corresponding to the fiducials and internal landmarks were recorded for each of the simulated films.

The differences between the coordinates of the fiducials in the real vs the simulated films were calculated to verify the accuracy of simulated patient location within the images. The averages and the standard deviations of these points were calculated. Also, as part of the registration, both the initial and final registered isocenter coordinates were recorded to verify the shift that is being reported and illustrated within the Offline Review.

Portal Images

The same radiographic phantom was used to create an actual and a virtual patient for testing the portal images. A plan was generated representing beams with a variety of different gantry angles. The phantom was again positioned on the treatment couch and aligned to the initial setup marks on the outside of the phantom. Portal images were taken at each of five different gantry angles. The phantom was shifted at the treatment machine to represent a patient setup error and all five portal images repeated. This was repeated a third time and all portal images repeated. A total of five gantry positions for each of the three different setup variations were taken for a total of 15 films were acquired on the phantom and were loaded into Offline Review. The coordinates of the fiducials in each of the images were recorded.

The initial CT images were anonymized to create another virtual patient in the VROC system. The same treatment plan was created on the virtual patient as for the phantom. Also, as was described regarding the virtual patient, the template DRR images were created to represent the different portal images. Using the VROC virtual treatment machine system, the set of 15 different portal films were created to simulate the portal images that were taken with the phantom. These 15 different images were loaded into Offline Review and the coordinates of the fiducials were recorded. The differences between the real and the simulated fiducial locations of the images were calculated to determine average and standard deviations between simulated portal images and real portal images.

CBCT Simulation

1. A treatment planning dataset was created to make a new patient. The patient file was exported to the treatment machine and the following five different setups and registrations were created.
2. Phantom aligned to correct location—imaged at correct location—registered to correct location (no shift and final alignment is correct).
3. Phantom aligned to correct location—imaged at correct location—shifted to a "wrong" location using the registration software. (Treatment location is incorrect).
4. Phantom aligned to wrong location—filmed at wrong location—registered and aligned back to correct location (shift and final alignment is correct)
5. Repeat of #2 (Images are correct, shifted off from isocenter—different direction)
6. Repeat of #3—Images are taken at incorrect location—shifted back to correct treatment location.

The five different alignment scenarios were performed on the radiographic phantom at the treatment machine. All sets of the registration images and the registration files were imported into the Offline Review system for verifications. The coordinates of the various fiducials were measured at both the acquired location as well as the registration location. A virtual patient was created to represent the same radiographic phantom that was used for the CBCT testing. This virtual patient was given a different name and a new plan was developed for this patient in the system. The initial CBCT dataset of the phantom was used as the template from which to derive all of the simulated scenarios. The same anatomical locations were identified and the coordinates recorded from the simulated CBCT dataset. The average and standard deviations of the differences in the coordinates were used to compare the actual and the simulated registration process.

Results

Treatment Dosimetric Errors

The daily treatment records were created for a test patient to include multiple fields treated and both under dose and overdose based on the number of MU given per each of the treatment beams. These files were imported into the VROC to verify that the dose recording based on the number and dose in the treatment fields matched the expected values. For the situations tested, the dose tracking matched the expected values. The simulation of a person overriding and typing in their credentials was not simulated in this initial development. This is a matter of identifying the correct field label within the DICOM header and making the appropriate changes to them. Additional modifications could be made for future work depending on the level of sophistication desired within the VROC. For the purpose of dose tracking, only the total fractions and the total dose were of interest at this stage in the development.

Daily Orthogonal KV Images

Figure 11:
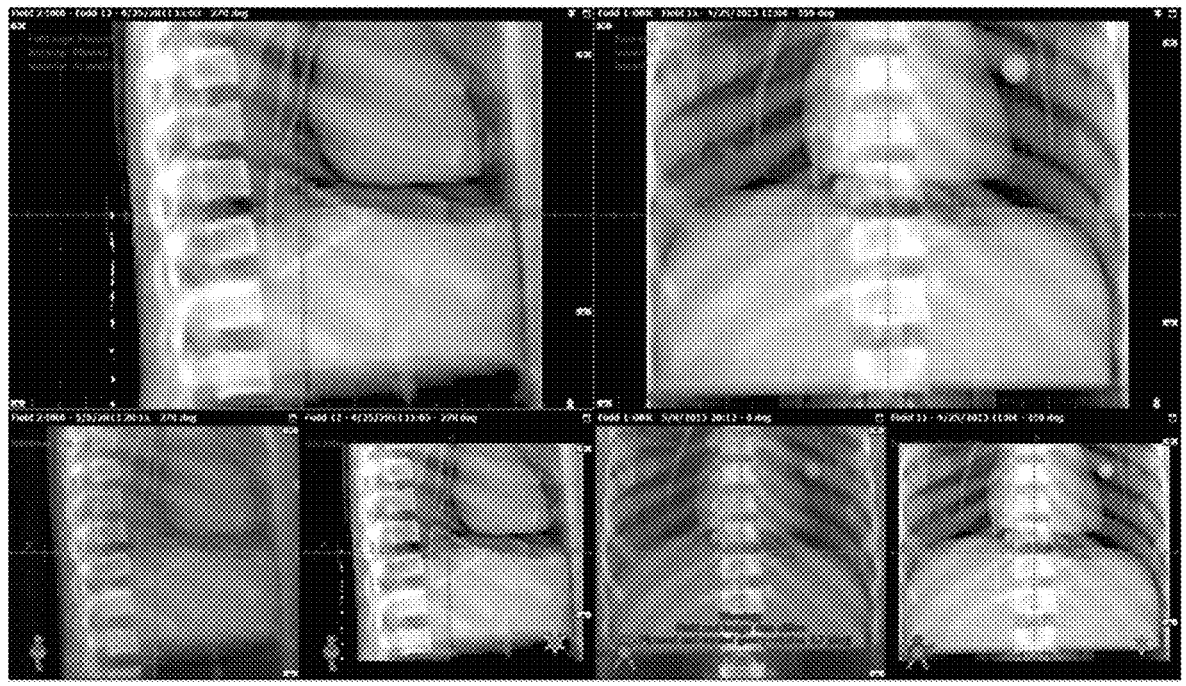
FIG. 11 is a figure demonstrating simulated orthogonal kV images without patient setup error.

In orthogonal kV imaging one image represents a beam entering from the anterior of the patient or an AP beam. The other beam represents a beam entering from the patient's right side and is called a right lateral. The right lateral beam indicates the patient offset in the superior/inferior directions (Y axis of the film) and the anterior/posterior direction (X axis of the film). The AP film indicates the left and right direction (X axis) and the superior/inferior direction (Y axis). FIG. 11 is an example of one of the simulated test pairs of films. The images on the left side are the Lateral images, and the images on the right side are the AP images. The main window for both images is a fusion of the registration image (ideal or expected patient location) and the simulated image, and the images in the bottom are the registration image (left) and the simulated film (right).

For each of the films, coordinates for five unique points were measured. Three of the points corresponded to the metal fiducials and two were for anatomical points representing a point on one of the vertebral bodies and a point in the left lung. Also the coordinates of the isocenter at the time the film was acquired and the isocenter after the registration were recorded.

Figure 12:
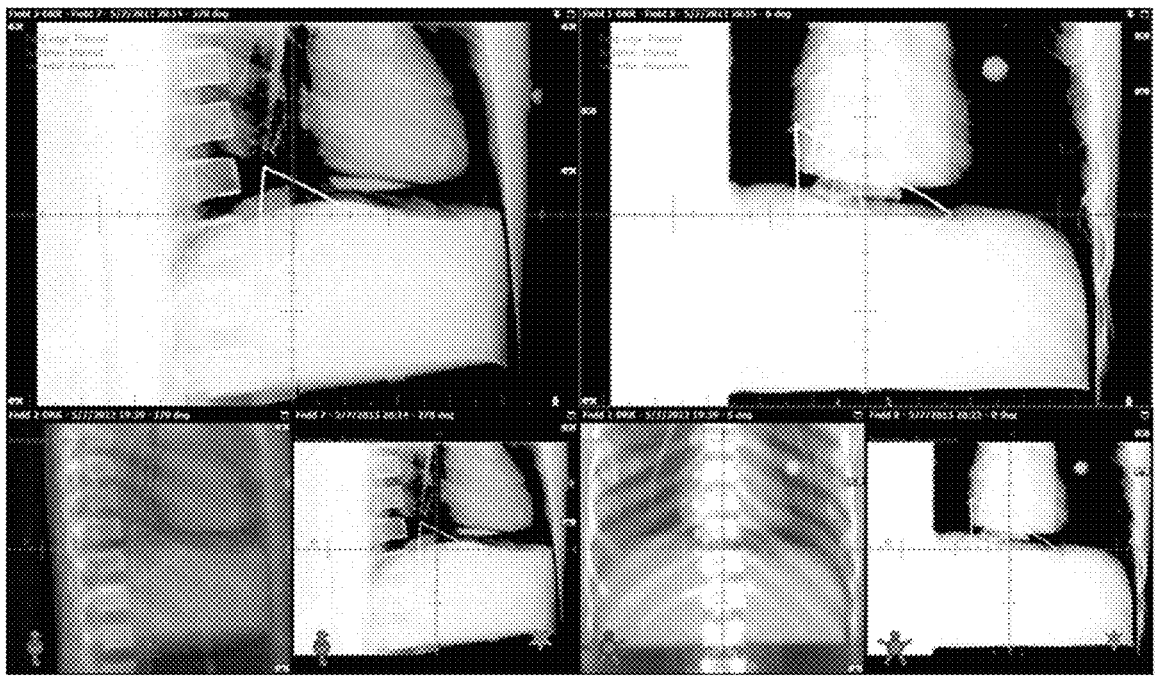
FIG. 12 is a figure of actual orthogonal kV images without patient setup error.

Initial check of the VROC system was that all of the simulated films could be loaded into Offline Review and were able to be displayed correctly. FIG. 11 is the simulated film setup that should mimic FIG. 12 (real) phantom setup. What can be noticed is that the image quality or window and level between images are not exactly the same, and the edges on the wire fiducials for the simulated images are blurry due to the reconstruction which is based on CT slice thickness.

Figure 13:
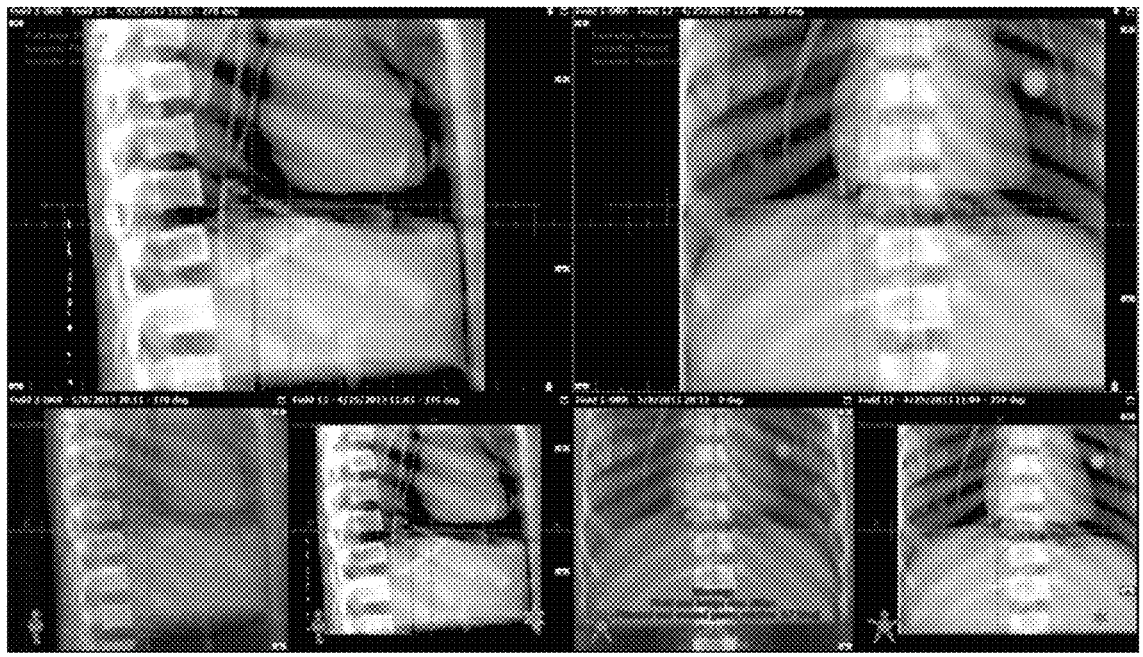
FIG. 13 is a figure demonstrating simulated orthogonal kV images with a setup error.
Figure 14:
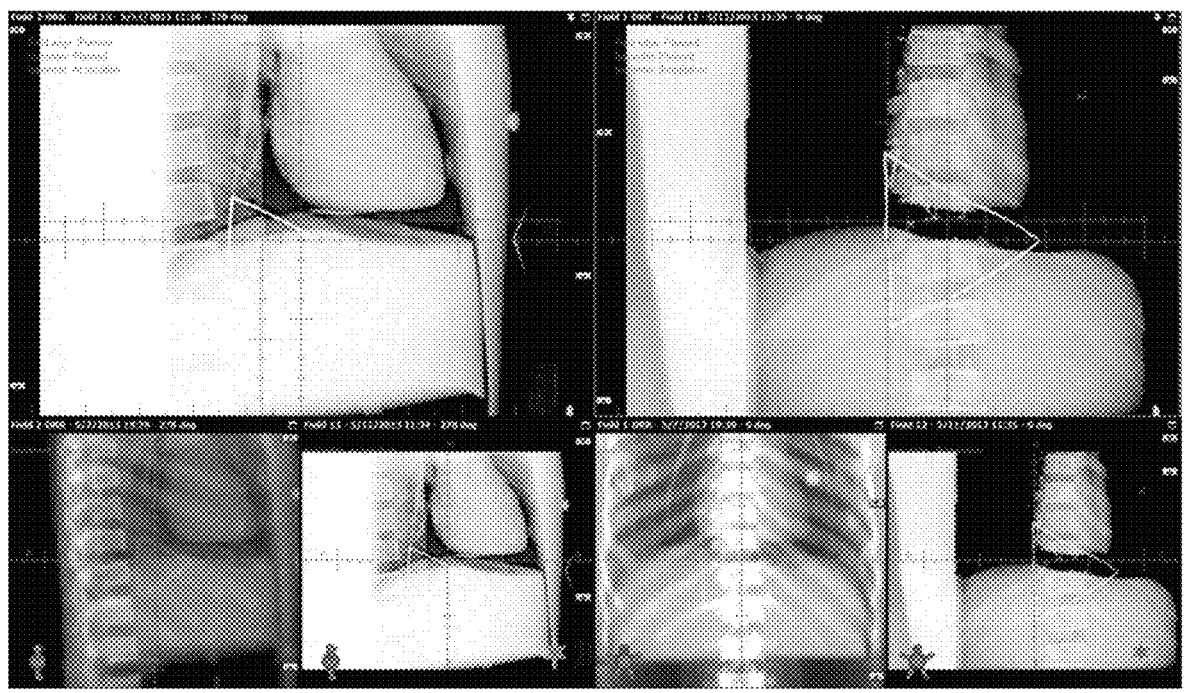
FIG. 14 is a figure of actual orthogonal kV images with a setup error.

When a patient is not setup correctly at the treatment machine and the therapists shift the patient after initial imaging, this is indicated by different colored crosshairs in the image in the Offline Review software. An orange crosshair indicates the location the patient was when the film was acquired and the green crosshair indicates where the patient was after image registration. This is illustrated in FIG. 13 for the simulated setup error and in FIG. 14 for the real setup error. Because the simulated films had to be manually shifted and cropped and also the registration file had to be modified to indicate a correction to the setup error, it was important to check the coordinates of the images as well as the coordinates of the two different isocenters.

To determine the overall accuracy of the simulated films compared to the real films the differences in the fiducials and isocenter points were taken. A total of 24 image pairs were available for evaluation, 12 "real" datasets and 12 "simulated" datasets. For each film, a total of 60 different data points were compared, along with the 12 acquired isocenter points and 12 actual isocenter points. The coordinates of the points were read out in pixel values and converted to mm. The pixel size of all films was 0.26 mm. The overall difference between real and simulated fiducial coordinates was 3.65±2.25 mm. The overall differences between real and simulated acquired isocenter were 1.94±2.80 mm and for the registered isocenter it was 0.89±0.81 mm. These values were calculated for each of the orthogonal directions and are listed in Table 5.

and standard deviation between the sets of image was 2.94±2.05 mm. Unlike the kV images, each film represents different patient orientation so there was no attempt to divide the data by patient orientation.

CBCT Verification Images

Figure 19:
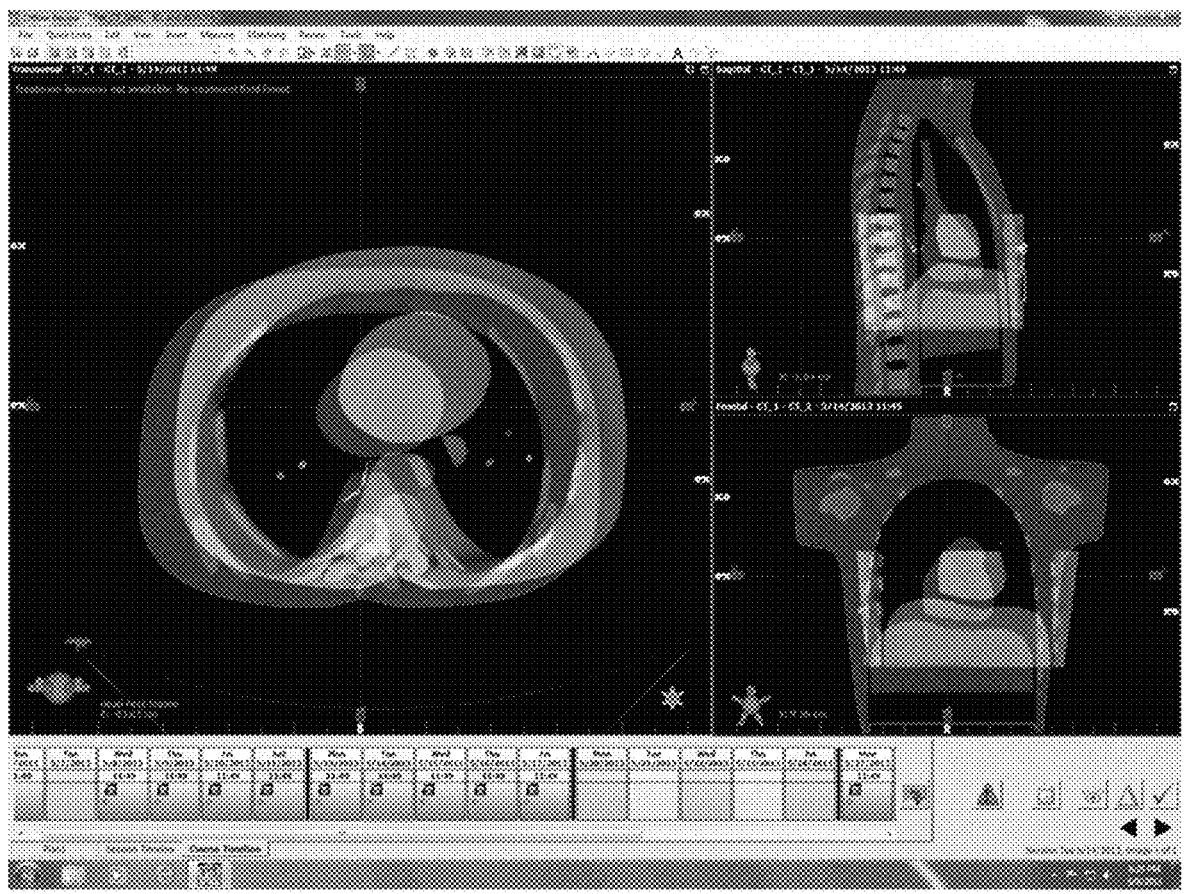
FIG. 19 is a figure depicting an example of a simulated CBCT image registration.

The CBCT data analysis within the Offline Review software was similar to the orthogonal image set in that the default review mode displays the CBCT dataset over top of the treatment planning CT representing the final position of the patient at the end of the registration process. An example of the CBCT image registration process is illustrated in FIG. 19. For each CT, a set of eight different points made up of fiducials and anatomical landmarks were used. For one dataset the shift caused two of the fiducials to not be included in the actual CT scan so for that pair of images, only six points were evaluated. The coordinates were based on the coordinate system of the treatment planning CT dataset that had a pixel size of 0.85 mm and a slice thickness of 3.0 mm. The average and standard deviation of the difference in actual and simulated images was 0.46±1.06 mm Lateral; 0.25±1.27 mm A/P; −0.33±2.07 mm S/I. (Included in Table 5).

TABLE 5

Difference between actual and simulated images

| Difference (actual vs simulated) | Overall avg. (mm) | AP mm | LAT mm | S/I mm |
|---|---|---|---|---|
| Portal images fiducials | 3.14 ± 2.21 | | | |
| kV fiducials | 3.65 ± 2.25 | 0.79 ± 1.67 | 1.25 ± 2.19 | 0.21 ± 3.20 |
| kV alignment isocenter | 1.94 ± 2.80 | 0.16 ± 0.36 | −0.09 ± 0.75 | 0.12 ± 0.31 |
| kV registered isocenter | 0.89 ± 0.81 | 0.05 ± 0.10 | 0.15 ± 0.56 | 0.16 ± 0.34 |
| CBCT fiducials | 2.49 ± 2.03 | 0.25 ± 1.27 | 0.46 ± 1.06 | −0.33 ± 2.07 |
| CBCT alignment isocenter | 0.78 ± 0.15 | −0.17 ± 2.15 | 0.85 ± 1.60 | 1.21 ± 2.71 |
| CBCT registered isocenter | 0.78 ± 0.15 | −1.21 ± 1.16 | 1.37 ± 1.15 | −1.21 ± 1.66 |

Portal Images

Figure 15:
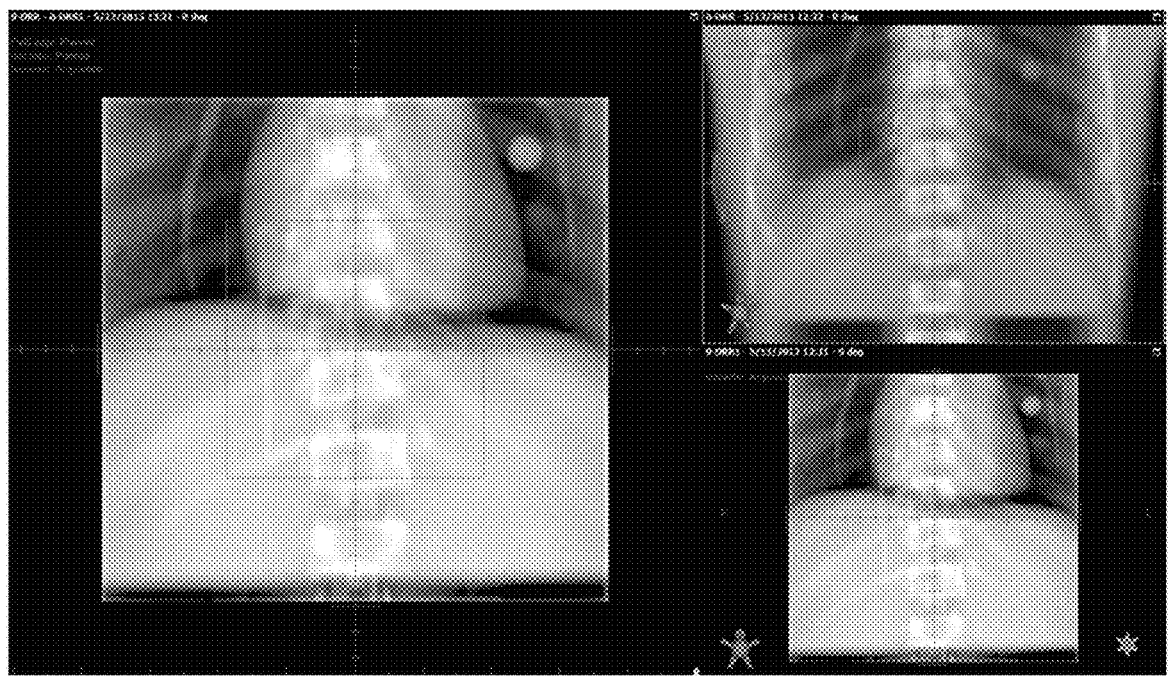
FIG. 15 is a figure demonstrating simulated portal film gantry at 0 degrees without patient setup error.
Figure 16:
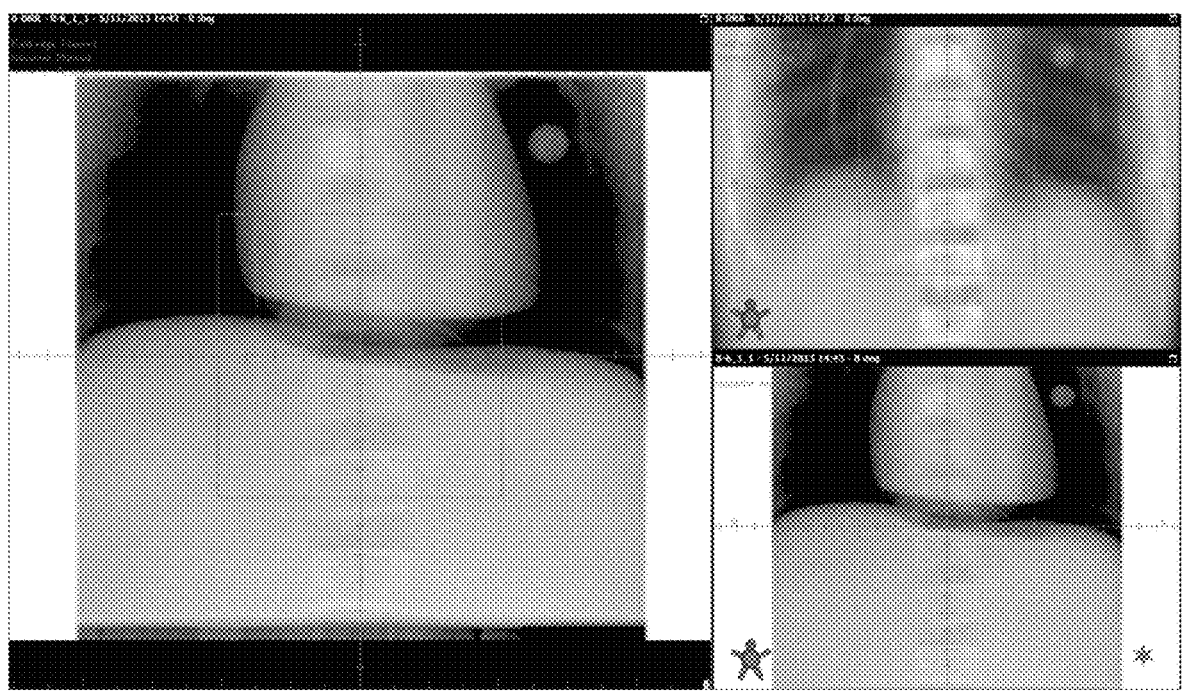
FIG. 16 is a figure of actual portal film gantry at 0 degrees without patient setup error.
Figure 17:
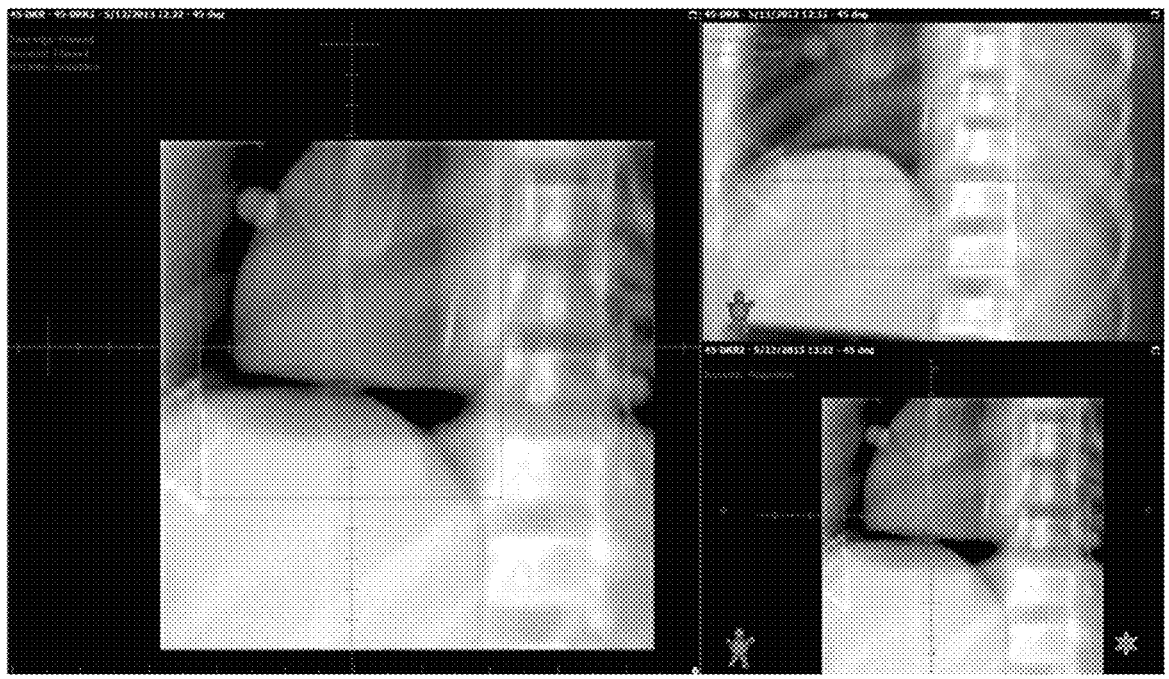
FIG. 17 is a figure depicting a simulated portal film gantry at 45 degrees with patient setup error.
Figure 18:
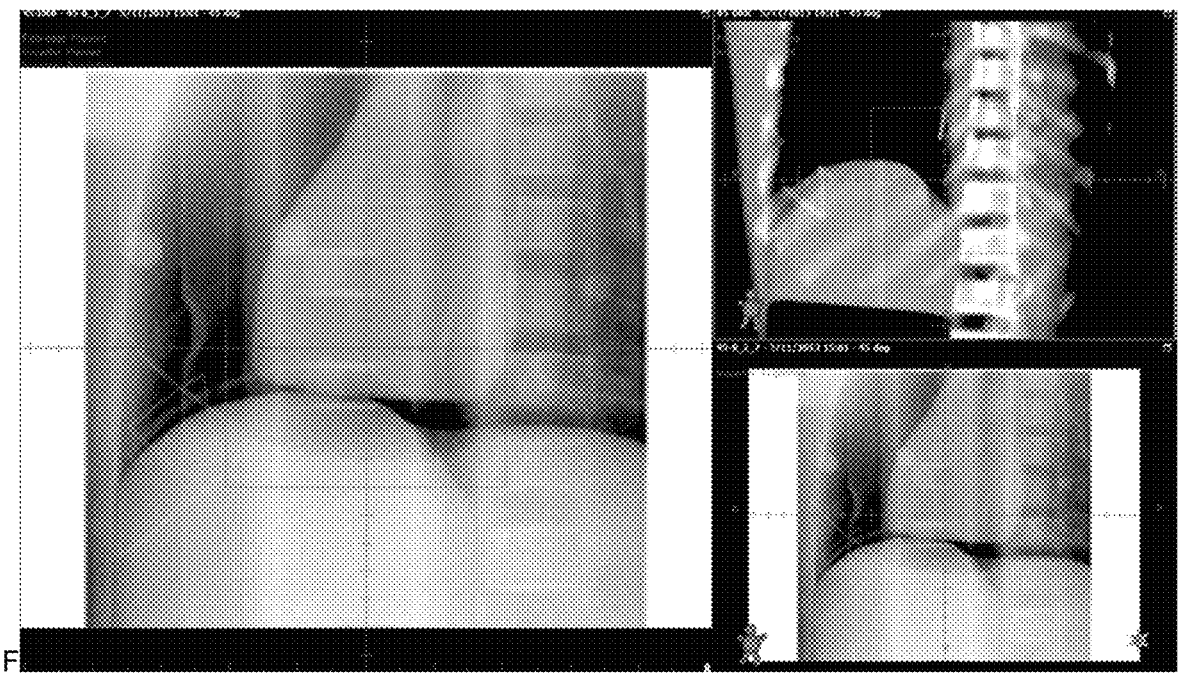
FIG. 18 is a figure of actual portal film gantry at 45 degrees with patient setup error.

FIGS. 15 and 16 illustrate the simulated (FIG. 15) and actual (FIG. 16) portal images for a phantom that is setup without errors for the beam with gantry angle 0 degrees. FIG. 17 and FIG. 18 are the simulated and actual portal images for the beam with gantry angle of 45 degrees with the phantom offset in all three orthogonal directions. Coordinates of several points within both the simulated and the actual portal images were recorded using the Offline Review application. These coordinates are relative to the center of each film and therefore can be used to determine the offset between the simulation and the actual images. For each image, between five and nine unique points either described by a metal fiducial on the phantom surface or anatomical landmarks within the phantom were used. A total of 15 different films with 5 different gantry angles were used to evaluate the code to simulate films. There was a total of 110 unique points that were compared between actual film and simulated film.

The overall distance to agreement was calculated from the shift coordinates and the average and standard deviations for all points was 3.14±2.21 mm. (included in Table 5). One particular simulated film for the gantry angle of 140 indicated the highest offset between simulated and created (due to difficulty in visualizing some of the fiducials in the real portal image). By eliminating these data points the average Conclusions Both dosimetric and spatial errors were simulated within the VROC system. Dosimetric errors typically occurred at the time of treatment planning and will be available as treatment plan options for the trainee to review before the virtual patient starts treatment. For errors involving dosimetric variance at the time of treatment, the file representing the treatment was modified to reflect different errors in dose or beam settings prior to importing into the VROC system. Spatial errors that occur at the treatment machine were detected by the use of patient verification images. The virtual radiation machine was a collection of MATLAB™ code that was created to create these verification files and to simulate the changes in these images if a spatial error occurred Validation was done to show that errors in the simulated images were the same as ground truth values of actual setup errors on a radiographic phantom.

The results show that for all three treatment imaging modalities, the code in the VROC virtual treatment machine generated images that could be successfully uploaded into the VROC to represent daily treatments. Careful attention to the DICOM header within the VROC code allowed the patient files to load and reference the correct set of images within the Offline Review software. These tests also indicated that the shifts of the images to represent patient setup errors could be made in the correct direction and made to represent the overall magnitude of a setup error.

Overall, the CT images showed better agreement in the location of the simulated error between simulated images and real images. In comparing the kV images and the portal images, the kV images have the advantage of being able to identify all three directions at one time. The agreement between the actual and the simulated films for all points was worse in the superior and inferior direction than in the other directions. The DRR that was used for the simulated film had a decreased resolution in this direction because the CT scan that was used to create the DRR was taken with a 3 mm slice thickness. When the DRR was created, the average pixel value between slices was used to create the image. It has been documented in different localization studies that the resolution in the Superior/Inferior direction is dependent upon the CT slice thickness. By using CT images with smaller slice width, this should improve. Localization studies using as small as 1.5 mm or less CT slice are often needed when treating very small areas such as brain treatments in order to improve the resolution in this plane.

Also of note is that the fiducial average and standard deviations are greater than those for isocenter or those for CT (anatomical points). This is related to an issue of divergence of planar imaging. Divergence, or penumbra occurs because the radiation beam fans out as it exits the x-ray machine, passes through the patient, and interacts on the imaging panel. The overall result is a magnification that increases with increasing distance from the center of the image. This magnification issue also increases with increasing distance from the imaging panel. Many of the fiducials that were used to compare the real films to the simulated films were on the surface of the phantom and were farther from the image panel that the actual treatment volume. As the fiducials are moved away from the center of the beam, the relative distance between them will become magnified.

The simulated film shifts do not account for divergence. It is important to note that the reference image that is used to calculate the patient setup error also does not account for this change in distortion. Therefore, when overlaying the images, the simulated images show a better agreement to the reference images than do the real images. The divergence issue is not as much of a problem for objects that are farther from the x-ray source or for objects close to the center of the beam. This is why the coordinates for the isocenter locations show good agreement between actual and simulated films.

This overall agreement between the simulated and the actual films for marks on the patient surface of about 3.0 mm may not be adequate for high-precisions treatment techniques, but are well within the normal margins for standard radiotherapy treatment. Studies have been done that indicate that the prostate can move anywhere between 5 mm and up to 10 mm during the time the patient is on the treatment table. It is not uncommon to see changes in patient anatomy due to tumor response to radiation. In head and neck cancer, tumor changes of up to 10 mm have been documents. These two examples indicate that a deviation on the order of 10 mm may be within clinical margins for the target and would not be counted as an error. For this simulation testing, the errors that were chosen were based on reported setup errors where the alignment was to the wrong vertebral body or to patient external marks. In these cases the setup error was on the order of 35 mm.

The purpose of these studies was to validate the virtual treatment machine software of the VROC. Treatment records can be created and uploaded to the VROC on a daily basis. These records can indicate a change in dose per fraction or total dose. The different types of images and their corresponding registration file can all be created and successfully uploaded into the VROC. If any of the tags within the DICOM header are not correct the files will not load into the Offline Review software. Setup errors on the order of 35 mm were tested within all systems. The simulated films were within 4 mm overall agreement of the actual films based on coordinates of fiducial points and within 2 mm overall for points in the center of the patient and near the isocenter.

Radiation Metrics and Radiation Errors

To investigate the details of how the metrics change specifically based on errors, a set of ten errors were simulated onto three head and neck cancer datasets. Within all three datasets the same normal tissues were contoured and the prescribed doses were the same. This study was done in order to investigate the details of the normal tissue metrics to determine which, if any, best described the overall effect of the errors on the patient risk of injury. Head and neck treatments were chosen because they are frequency treated so there are a number of different cases, and because of the anatomy they remain one of the more complicated treatment sites in most radiation oncology clinics and more complex treatments have been associated with either a higher incidence or for more severe consequences from errors.

The three patients had been treated with IMRT treatment to the primary target and involved neck nodes to 70 Gy, while simultaneously treating the secondary lymphatic nodes to 63 Gy, and the contra-lateral lymphatic nodes to 57 Gy. For the low-neck region, a single anterior field was used to treat lower neck to 50 Gy using a midline block, as needed, to spare the cord. The upper and lower fields were matched by using a single isocenter and asymmetric jaws.

A total of ten different errors were simulated. Four of them were geometric setup errors occurring between 2-5 different treatments out of the 35 total treatments. Four of the errors were dosimetric and occurred primarily at the time of treatment planning. The final two were a combination of both dosimetric and spatial errors.

A second study was conducted to evaluate changes in metrics with different anatomy and prescription doses over a range of different treatment types. Because the anatomy and the prescribed doses could change from one case to another, the recommended metrics should be applicable over all cases that would occur within the VROC. Ten unique datasets to different disease sites were selected and three different errors were simulated onto each. The errors that were selected were based on the likelihood of occurrence, but were modified slightly to create metric sets that would include all levels of severity. For each patient, the metrics for the errors and the standard plans were calculated.

Metric Calculations

The metrics were calculated based on the DVH from the composite treatment plan. The details about the metrics and details about the developed code are discussed in greater detail above. A complete list of all of the metrics that were calculated is included in Table 6. The metrics were calculated for the error plans as well as for the standard or "as treated" plan. The difference and percentage change between the standard plan and the error plan for each metric was also calculated.

TABLE 6

Data calculated
All data collected for cases

PTV values

| | |
|---|---|
| (1) | Volume (cc) |
| (2) | EUD |
| (3) | TCP |
| (4) | Mean dose |
| (5) | Coverage by Rx line |

Normal structure (n)

| | |
|---|---|
| (6) | EUD (n) |
| (7) | NTCP (n) |
| (8) | Normal CC > Rx |

Combined

| | |
|---|---|
| | J (from line 1, 5, and 8) |
| | DD (from line 2 & 6) |

All of the probabilities metrics (NTCP and TCP) that were calculated were combined using mathematical combinations in order to calculate both a probability of complication free survival, P+ which was calculated from the combined $NTCP_{tot}$ and the TCP. The combined $NTPC_{tot}$ represent the percentage likelihood of any complication from any structure.

Detrimental dose (DD) as described above is a number that is related specifically to errors in radiation oncology. It is calculated by weighting the dose differences to different structures because of the error by the relative sensitivity of each structure. For the purposes of this study, the dose differences to each structure were taken from the change in the EUD for each structure.

Error Scoring

One of the goals of the metric calculation analysis was to be able to correlate the metric scores to overall severity of the error. There is currently no consensus on severity scoring nor is there a national radiation error reporting system. Newly published recommendations for a standardized national error reporting system include two different error-scoring systems. These were described (Table 7 and Table 8). One is based on dose severity determined by the percentage change in dose to any structure. The other is a consequence severity, based on expert opinion and on the grade of different side effects from the error. Ideally, a set of metrics that could automatically predict these scores would be useful for feedback from the VROC system.

TABLE 7

Dosimetric severity score

| Score | Dosimetric Scale |
|---|---|
| 9/10 | >100% absolute dose deviation from the total prescription for any structure |
| 7/8 | >25-100% absolute dose deviation from the total prescription for any structure |
| 5/6 | >10-25% absolute dose deviation from the total prescription for any structure |
| 3/4 | >5-10% absolute dose deviation from the total prescription for any structure |
| 1/2 | <5% absolute dose deviation from the total prescription for any structure |
| | Not Applicable |

Adapted from Ford EC, Fong de Los Santos L, Pawlicki T, et al. Consensus recommendations for incident learning database structures in radiation oncology. Med Phys; 39 p. 7285 Appendix 1 Table 1.

For the dose severity score, the percentage of EUD change between the error plan and the as treated plan was used. The recommendations for this dose severity scoring are based on the maximum percentage change in the dose to any structure. There are no specific recommendations in the report on how these should be normalized. For simplification and consistency, the percentage EUD changes were normalized to the prescribed dose. Both increases and decreases in target dose are considered and only increases in doses to normal tissues are considered. The maximum of all of these percentage changes in EUD was then used to determine the dosimetric severity score.

TABLE 8

Consequence severity score

| Score | Consequences (actual or predicted) |
|---|---|
| 10 | Premature death |
| 8/9 | Life threatening - intervention essential. |
| 8 | Possible recurrence due to under dose |
| 7 | Permanent major disability (or Grade 3/4 permanent toxicity) |
| 5/6 | Permanent minor disability (Grade 1/2 permanent toxicity) |
| 3/4 | Temporary side effects - Major Treatment/hospitalization |
| 2 | Temporary side effects - intervention |
| 1 | Temporary side effects - no intervention |
| 0 | No harm |
| . . . | Unknown |

Adapted from Ford EC, Fong de Los Santos L, Pawlicki T, et al. Consensus recommendations for incident learning database structures in radiation oncology. Med Phys; 39: p. 7285 Appendix 2 Table 1.

For the consequence severity metric, all sixty of the dose errors (thirty head and neck errors and thirty variety of disease sites) that were calculated were evaluated by experts in radiation oncology (two physicists and one physician) who gave a score using Table 8 along with clinical experience to predict the consequences. To score the severity of the errors, the experts had access to the different EUD values, change in coverage of the target structures, changes in both EUD and NTCP to normal tissues, and a complete description of the error. A cross section of the patient anatomy and treatment plan was also included to help to describe the region of the patient that was treated. In some cases the expert could make an estimate of the severity based completely on their knowledge of the anatomy involved and not based on the specific data presented.

Results

Contouring Metrics

The contour metrics feedback calculations were compared to volume calculations from within Eclipse™ along with hand calculations for the similarity metrics. A test case with several different geometrical shaped structures (cube, sphere, single slice square) was created. The volumes of the structures calculated in Eclipse™ were compared to those calculated using the VROC contour comparison code. The agreement was within 5% for all structures that were >1cc. The small structure volume was calculated as 0.7 cc in Eclipse™ and 0.9 cc in VROC. To test the Dice's similarity calculation, the target structures were copied and changed to create overlap, under lap and mis-alignment of the object. Volume calculations within Eclipse™ were used to get information needed to perform hand-calculation of the Dice's similarly metric. Three different scenarios were tested and the VROC Dice's similarity metric was within 2% of hand calculation.

Error Scoring

The primary goal of investigating the metrics was to determine if there would be a way to automate both the dose severity and consequence severity score by using the other metrics that were calculated. The dose metric from Table 7 scales with dose, but is not linear. Since this is directly related to the change in dose to any structure the values from within the table were plotted to determine an equation to be used for automatically calculating the dose severity metric based on the percentage change in EUD. A logarithmic fit to the published table yielded Equation 6-1.

$$\text{Dose Metric} = 1.85 * \ln\left[\frac{\% \ EUD}{0.7}\right] \quad (6\text{-}1)$$

Equation 6-1 was included into the metric feedback calculations so that the dose metric could be obtained automatically once all of the % EUD calculations are made.

Three different experts in radiation oncology evaluated the different error plans to determine the consequence severity score of the different plans. The average and standard deviations of all of the scores was calculated to be used to compare the various different other metrics. Initial observations of both datasets indicate that within the errors that would fall between 2 and 7 there is a greater variability in expert score than for errors with "no effect=0" and those that would definitely cause "serious harm or death=10".

Over all sixty errors reported, the mean standard deviation was 1.38. Upon further investigation one problem with this scoring system is the non-linearity that is introduced because of the recommendation to score a "possible recurrence due to under dose" as an "8". The values that were rated with an 8 were then taken out of the analysis and the average standard deviation in the scores improved to 1.16.

The under-dose errors were evaluated separately. In total there were 35 different cases in which the target % EUD decreased with the simulated error. Of these, only 17 were rated by any one of the three raters as an 8. Of the 17, about half showed complete agreement between the three evaluators. For those in complete agreement the minimum absolute % EUD change reported was 12.6%. For those in which there was not agreement the average under dose was 4.4%. Of those cases where the EUD decreased, but the error was not scored as an 8, the change in target EUD was <5%.

Also associated with an under-dose is the percentage of the target that is covered by the prescription line. The average change in percentage coverage for all of the 17 under-dose cases was 53% (14% min). For those that were not in agreement the average was 38%. Of those cases where the EUD decreased, but the error was not scored as an 8 the average change in coverage was 4%. For automation of the consequence severity score, a cutoff rule was selected such that any target dose decrease of 5% along with a percentage coverage loss of 10% would be reported as an 8 in the initial VROC feedback.

The averages and maximum values of the consequence severity scores from the three raters were compared to the dose severity score calculated by Equation 6-1. This was to determine if the dose severity score could be used as an approximation to the consequence severity score. For all 60 cases, least square regression was used to compare each of the three rater's scores, the average and the maximum scores to the dose severity metric. The best correlation between dose severity metric and any of the consequence severity metrics was found for the average inter-rater score ($R^2$=0.675) Analysis without the 17 under dose cases improved ($R^2$=0.818) compared to an individual rater of $R^2$=0.790. This indicates that the dose severity score can serve as a guide for the consequence severity score.

Metric Analysis

Head and Neck Data Comparison

The metrics from the head and neck cases were first investigated to determine how best to report the different metrics and to observe general trends in the data. A sample of the metrics for the standard plan (without errors) and two plans with errors are shown in Table 9 for illustration. The dose severity score and the consequence severity score that were given to these plans are included in this table for comparison. These samples were chosen because the errors had a severity scores >0. The plan listed as Error 1 represents a spatial error in which the patient setup was approximately 3 cm different from the desired location for 2 of the 35 treatments. Table 9 reports a spatial error in which the patient was aligned to some other external marks that were on the patient instead of the ideal location. For this example, the patient was set to the wrong isocenter for 5 of 35 treatments.

TABLE 9

Example of calculated metrics for a single head and neck case

| Metric | Baseline | Error 1 | Error 2 |
|---|---|---|---|
| Prescribed dose (Gy) | 70 | 70 | 70 |
| # Fractions | 35 | 35 | 35 |
| # Error fractions | 0 | 2 | 5 |
| Dose severity metric |  | 1 | 5 |
| Consequence severity metric |  | 0 | 6 |
| EUD PTV1 | 75.75 | 75.17 | 71.10 |
| % Coverage by Rx | 97.09 | 96.09 | 68.20 |
| CI (J) | 0.74 | 0.75 | 0.61 |
| EUD brainstem (Gy) | 22.24 | 22.16 | 22.33 |
| NTCP brainstem (%) | 0.00 | 0.00 | 0.00 |
| EUD ipsilateral parotid (Gy) | 46.31 | 47.07 | 47.91 |
| NTCP ipsilateral parotid (%) | 52.72 | 59.13 | 65.74 |
| EUD contralateral parotid (Gy) | 19.73 | 20.97 | 24.25 |
| NTCP contralateral parotid (%) | 0.00 | 0.00 | 0.00 |
| EUD rt eye (Gy) | 1.64 | 2.37 | 7.69 |
| NTCP rt eye (%) | 0.00 | 0.00 | 0.00 |
| EUD lt eye (Gy) | 1.12 | 1.53 | 5.35 |
| NTCP lt eye (%) | 0.00 | 0.00 | 0.00 |
| EUD larynx (Gy) | 20.61 | 21.67 | 23.78 |
| NTCP larynx (%) | 0.00 | 0.00 | 0.00 |
| EUD oral cavity (Gy) | 57.97 | 58.62 | 57.98 |
| NTCP oral cavity (%) | 0.57 | 0.69 | 0.58 |
| EUD spinal cord (Gy) | 34.66 | 34.57 | 34.80 |
| NTCP spinal cord (%) | 0.06 | 0.06 | 0.07 |
| Combined risk (%) | 53.02 | 59.43 | 65.96 |
| DD (Gy*) | 0.00 | 27.22 | 113.80 |

Two of the first observations that were made with the data were related to the mean target dose and to the TCP that were initially calculated. The mean target dose, for most purposes was redundant with the target EUD dose and therefore it was eliminated from reporting. It was, however, useful to check that the EUD calculations were being performed correctly for initial calculations. The second observation was related to the tumor control probability (TCP). This value should be related to the likelihood of tumor control and should approach 100% for a better control rate. The initial calculations of these values yielded unexpectedly low numbers for the standard plan, even though they were clinically acceptable plan that would presumably have good tumor response. For the three clinical head and neck plans, initial TCP values were 65.2%, 58.7%, and 61.3%. Another issue with using this metric was that it increases (or improves) for all increases in dose, therefore, for any over-dose; the TCP will appear to improve. For these reasons, TCP was not recommended for final reporting. Because the TCP was not included the P+ values that were proposed (combined probability) were also not used for further analysis.

For target volumes, the EUD to the target appears to be a good indicator of the overall dose to the target structure. This metric and the percentage of target volume covered by the prescription line are indicators of the target receiving adequate dose. For the examples in Table 9, shows that only 68% of the target volume received the prescribed dose when this error occurred. This could be a useful in describing a lack of tumor control.

To also check that the changes in EUD were not overly sensitive to specific patient anatomy, the same ten errors were duplicated on a total of three different head and neck patients. The average standard deviation for all target EUD difference was 1.3 Gy out of the prescribed 70 Gy or <2%. The worst EUD correlation between the three patients was with one particular error where one field was treated for extra fractions. The standard deviation between the 3 patients was 10.1 Gy and indicates that for this particular type of error the difference in EUD could vary greatly from one patient to the next. In general, the EUD differences were not sensitive to specific patient anatomy for the same type of target, for the same type of error.

The conformity index (J) is related to the target volume and to the overall tissue volume receiving the prescribed dose. A low conformity could indicate either a miss of the target, an over-dose, or an under-dose. In the examples in Table 9, the change in the overall conformity was worse for the error that occurred for five treatments than for the one that only occurred twice. Initial observations indicate that the conformity index appears to change for all different types of errors, including dosimetric errors as well as spatial errors.

In order to consider possible harm done to the patient due to the error, the NTCP and EUD for each of the normal structures were evaluated. Normal structures included in the head and neck cases included: brainstem, spinal cord, parotid glands, larynx, oral cavity, and eyes. Upon closer examination, the only normal structures for which the NTCP was greater than 1% for either the normal plan or the error plan were for the structures of ipsilateral parotid and spinal cord.

Relative to the parotid gland doses, only one of the three patients had high values of NTCP. This patient had an NTCP value of 48.8% for the standard plan. The other two patient NTCP values were <5% and indicate that the NTCP values are sensitive to specific patient anatomy and treatment plan. Another observation was that the change in NTCP would be greater if the NTCP is already high. This is the case for the patient illustrated in Table 9. The NTCP is already very high indicating the patient will likely suffer side effects to the parotid gland. Any changes to the plan due to errors will likely increase either the severity of those side effects or increase the likelihood of the side effects more so than for a patient that has an initial plan NTCP close to 0%. These observations indicate that side effects from errors cannot be generalized over different patients for the same tumor type and error.

A similar observation was seen for the NTCP values for the spinal cord. These values were minimal for all situations except for one significant error in which the spinal cord would have received a potential dose increase above threshold of 45Gy. Again the initial observations indicated that for only one of the three patients did the NTCP change enough to indicate a significant risk of injury.

Initial observations indicated that it may be useful to combine the NTCP values to eliminate reporting the structures that had NTCP values less than 1%. In order to create a simplified set of reported values, a combined $NTCP_{tot}$ could indicate whether the trainee should be concerned with looking into patient side effects. There is an added benefit in combining the NTCPs for comparing errors that occur on different patients with different normal structures from each other.

Initial observations of the changes in EUD to normal tissues were done to help to determine the overall magnitude of the error. The dose severity metric is based on the maximum percentage of change of dose. For these purposes, the EUD dose was normalized to the prescribed dose. For example, the right eye dose for Error 1 (Table 9) changed from 1.64 Gy to 2.37 Gy. This could either be calculated as an increase in 45% relative to the standard plan or a change of 1% of the overall dose (0.7 Gy out of 70 Gy prescribed dose). For comparing different plans and errors all EUD dose differences were normalized to the prescribed dose to determine how significant of a dose change occurred.

The final metric that was proposed was the Detrimental Dose (DD). The DD was calculated as a possible means of scoring or ranking the severity of an error and appears to scale according to the severity of the overall error. While the magnitude of the DD increases with an expected increase in severity of an error it is unclear how it relates to actual perceived severity or how it relates to physical dose.

Multiple Patient Metric Analyses

Unlike the head and neck study, the patients in this study were each treated to different prescribed doses and included different normal structures. Because there are also different number and types of structures for all patients only the combined metrics and normalized metrics could be compared. This included the percentage EUD changes, change in Conformity (J), $NTCP_{tot}$, and DD along with the severity scores given to each of the different treatment plans.

Combination of all Error Sets

All of the data for both studies was combined to determine if any of the calculated metrics could be used to within the VROC in order to recommend a consequence severity score that would correlate to expert scores. As already indicated, the consequence severity metric associated with under dose (score of 8) can automatically be calculated based on a threshold of 5% change in target EUD and change in dose overage of at least 10%.

The remaining analysis was to determine which of the metrics would best approximate the consequence severity score. Because the VROC will include patients with different anatomy and planned to different doses, the analysis focused on metrics that could be normalized and combined metrics that eliminate patient specific anatomical calculations. Linear regression analysis was performed on all data that could possibly be related to the severity. This included target EUD (Gy), % Change in target EUD, % target coverage, J, $NTCP_{tot}$, and DD. In addition to each of these values, the differences between these values and the standard plan values were also evaluated.

Figure 20:
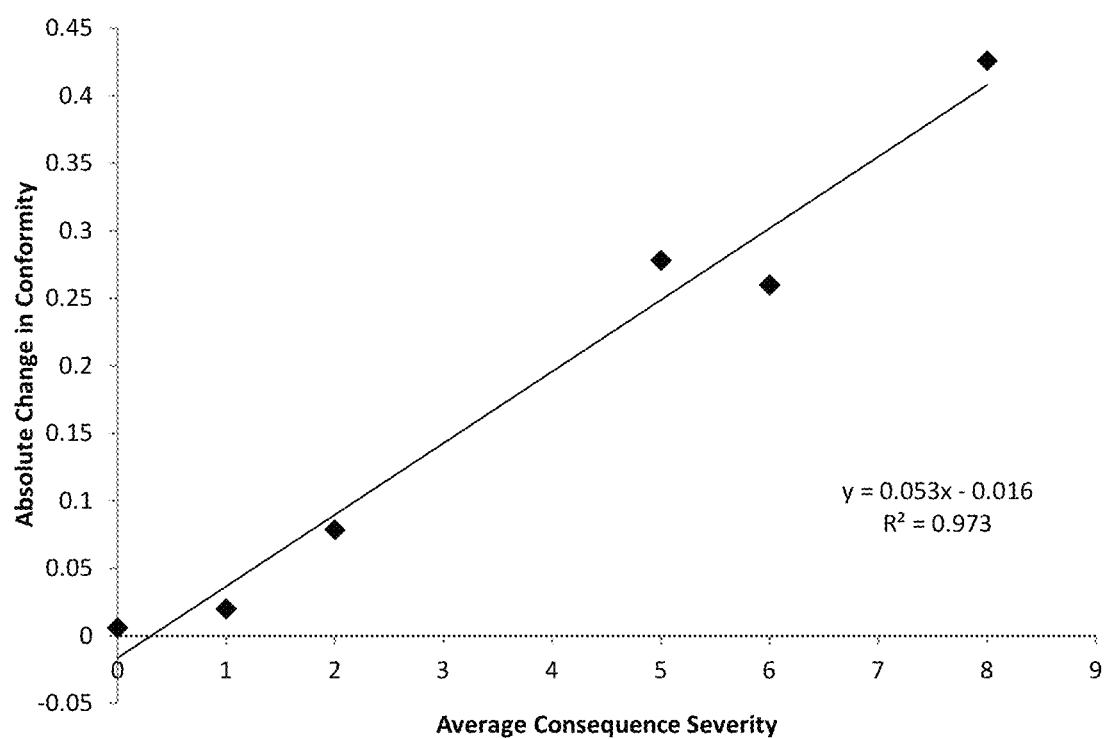
FIG. 20 is a figure depicting the absolute change in conformity vs average severity score.

A total of 43 of the original 60 error plans were evaluated (the under-dose plans were not included). Based on linear regression between the average consequence severity score and each of the different reported metrics, the metric with the highest correlation to the average severity score was the change in J. with a correlation of $R^2=0.467$. The datasets were sorted by the average severity metric to determine trends in the metrics. Table 10 is the average for each metric grouped by severity. Some of the severity scores were combined due to the relatively few errors with their values. By grouping the values based on natural cutoffs the change in the conformity fit the consequence severity score with a correlation of $R^2$ of 0.92. The graph representing the change in conformity index with severity score is included in FIG. 20.

TABLE 10

Average consequence severity vs average combined metrics

| Average severity | Avg. $NTCP_{tot}$ Dif | Avg. CI Dif | n (points) |
|---|---|---|---|
| 0 | 0.01 ± 0.02 | −0.01 ± 0.03 | 10 |
| 1 | 0.00 ± 3.04 | −0.02 ± 3.04 | 9 |
| 2 | 0.09 ± 3.66 | −0.08 ± 3.66 | 7 |
| 5 | 3.76 ± 3.61 | −0.28 ± 0.20 | 5 |
| 6 | 28.64 ± 29.75 | −0.26 ± 0.22 | 7 |
| 8 | 24.81 ± 37.78 | −0.43 ± 0.29 | 5 |
| $R^2$ | 0.71 | 0.92 | |

CONCLUSIONS

In the training of radiation oncology residents there is very little opportunity for the resident to learn from their mistakes or those of others. One of the key requirements for the VROC was that it allows errors to occur in order to provide opportunities to investigate how errors affect patient treatment. Additionally, there are very few quantitative metrics that can be used to either score the severity of an error that occurs or to evaluate a trainee regarding their ability to manage a patient. By evaluating a set of possible metrics that are associated with radiation therapy, we have identified a simplified set of metrics to use as feedback for the VROC system.

Contour metrics can be easily calculated by comparing two separate structure set files. The Dice's similarity metric and the calculated volumes and percentage values were tested for accuracy which indicates that the code was functional. Further testing could be done to test the overall usefulness in evaluating there metrics as they relate to errors.

The remaining study focused on the metrics associated with the composite treatment plan. The metrics were compared to a scoring system that is being implemented for a national radiation error reporting system. The scoring system includes a dose severity score and a consequence severity scores. One result of the study using three evaluators to score different treatment errors indicated that the scoring system may be prone to inconsistencies in how different experts score different errors.

As part of an additional study, it may be useful to better describe the values associated with the different scores in order to improve the consistency. Listing specific temporary and permanent side effects or describing specific interventions that can be used to treat the radiation-induced side effects could help provide standardization. A possible study of interest to further investigate this scoring system would be to have more experts score the errors and in addition provide feedback about the specific toxicity that caused them to rate the error with a particular score. Based on this information, the scoring system could be changed to better describe the consequences of a radiation error.

With respect to the target volume metrics the following two conclusions were made. First, the calculation of the TCP is not useful in comparing errors since it appears to improve with errors. Another reason not to use TCP is that for relatively low doses such as palliative care, the TCP is not meaningful. Second, the changes in EUD with different errors on a common disease site indicated that the change in EUD with errors is not sensitive to patient specific anatomical changes and serves as a good indicator for the overall plan dose change.

A non-linearity in the consequence severity score was noted for target volume under dose. For the VROC an under-dose in the target will be calculated by a decrease in the target EUD. A consequence severity score of "8" will be scored for an error if the target dose decreases by 5% and the target coverage changes by 10%. Overall, more testing must be done to determine specific cutoff values, but this would require additional validation of the expert scores.

The remaining analysis was done to try to describe the relative risk to normal tissues as a result of the error. Historically, errors were reported primarily based only on the change in target volume. The state of Florida has changed the required reporting guidelines to include any error that "will result in unintended permanent functional damage to an individual's organ or a physiological system, as determined by a physician" (from Florida Administrative Code 64E-5.101). The physician needs tools to help them to determine if an unintended permanent functional damage would occur as a result of the error.

The $NTCP_{tot}$ is theoretically useful to determine if there is an increased risk to the patient as a result of an error. Changes in $NTPC_{tot}$ could indicate that the physician should investigate further to determine which structure is most at risk. There were two specific issues with the correlation of $NTCP_{tot}$ to the consequence severity score. The first was an issue with the scoring system itself, which was already described. The second was that for some plans such as palliative cases, there were not enough structures contoured around the target volumes in order to represent the error. For consistency, all of the tissue surrounding a target volume, including unspecified soft tissue and bone would need to be consistently defined from one patient to the next so that all patients will have structures near the target volume from which to calculate NTCP. To better improve the correlation, this study should be repeated with all normal structures contoured on all datasets and all structures included in the NTCP calculations.

A similar problem to that described for the NTCP calculation was observed for the detrimental dose. The DD could possibly be a good indicator for the overall severity of the error. Theoretically, the weighting of different structures by the sensitivity as well as the dose change would appear to correlate with the actual perceived severity of the error. The data analysis from this study did not indicate this correlation. This was most likely due to the variety of different normal tissues used in the calculation. In order for this metric to be correlated to a health physics concept the overall burden on the patient must be considered. All of the irradiated volume must be accounted for in one of the structures in order for the calculation to scale appropriately for a variety of cases.

Lastly, the metric that was surprisingly well correlated to the consequence severity score was the conformity index (J). This is a calculation of how well the prescription volume matches the target volume. This metric is sensitive to both dosimetric errors as well as spatial errors. Conformity also changes for both under-dose and over-dose situations. Additionally, the metric itself is normalized between 0 and 1 making it easier to compare over all diseases and prescribed doses. The average change in J was correlated to the average consequence severity score in order to provide an equation that could be used within the VROC feedback code. By using this equation, a consequence severity metric can be calculated in the VROC. It is important to note that the error bars are very large on this metric, and the correlation was not strong, therefore this severity score is only a recommendation and is for educational purposes only.

An examples of the recommended VROC feedback includes a complete example of an error and how the feedback metrics can be used for an error study. The output from the VROC feedback report include the prescribed dose, the change in EUD to the target volume, dose and consequence severity metrics, change in conformity, and change in NTCPtot. A second table report indicates all target and normal tissue EUD and NTCP values. While the severity scores given in this report are "recommendations" generated by the VROC system, it will be part of the exercise for the trainee to determine their own recommended severity scores when completing the root cause analysis.

Acceptance and Validation

Figure 21:
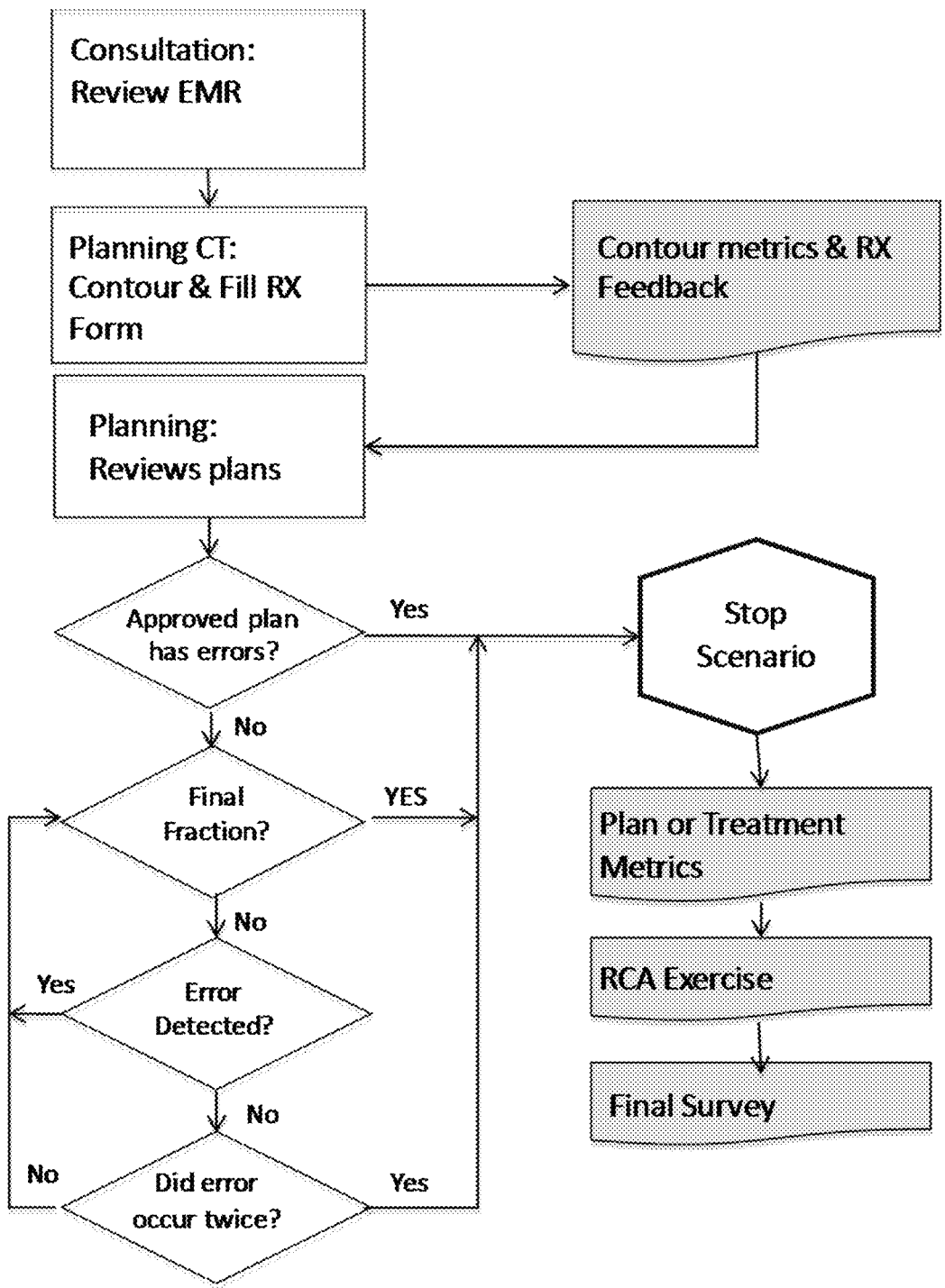
FIG. 21 is a flow diagram of a virtual radiation oncology clinic specific workflow for a single trainee and single virtual patient.

After the acceptance test was completed, a validation test was performed to evaluate the overall realism of the VROC. Five different users were asked to evaluate the VROC by reviewing two different virtual patients through the entire RO process. Each of the different primary functions of the simulated RO workflow was evaluated relative to realism and to the utility of the feedback given. A workflow diagram specific to the trainee within the VROC system was used to help navigate those completing the validation test through the VROC system. FIG. 21 is the diagram indicating how a trainee would manage a virtual patient through the VROC.

The five users were medical physicists with a variety of experience in radiation oncology. After viewing the two cases within the VROC system they were asked to fill in a survey of overall impressions of the VROC. They were also asked to make comments about the system including recommendations for improvements.

Based on the five users that initially evaluated the VROC, the most realistic aspect of the VROC is the contouring and pre-planning step, and the least realistic aspect was the consultation. This does not present a problem because this version of the VROC was not intended to fully simulate the consultation. Comments from the initial evaluation of the VROC indicate that one aspect of the VROC that was perceived as being useful or that was liked the best was the RCA exercise.

We claim:

1. A method of radiation oncology training performed by a virtual radiation oncology clinic (VROC) computer system that simulates an entire course of radiation therapy including an evaluation of a virtual patient by a trainee, an identification by the trainee of all therapeutic target and non-target regions of the virtual patient, a recommendation by the trainee of radiation doses to structures of the virtual patient in one or more treatment fractions, delivery of the recommended radiation closes in one or more treatment fractions to the structures of the virtual patient in accordance with the recommendation, and a follow up by the trainee with the virtual patient after delivery of all treatment fractions, the method comprising:
(a) with a computing device of the VROC computer system, reading an electronic medical record associated with the virtual patient from a database of the VROC computer system,
(b) with a computing device of the VROC computer system, causing the electronic medical record to be displayed to a trainee on a display of a user interface of the VROC computer system,
(c) in a computing device of the VROC computer system, receiving an electronic treatment plan associated with the virtual patient from the trainee, the electronic treatment plan including the identification by the trainee of all therapeutic target and non-target regions of the virtual patient, the recommendation by the trainee of radiation doses to structures of the virtual patient in one or more treatment fractions, and the delivery of the recommended radiation doses in one or more treatment fractions to the structures of the virtual patient in accordance with the recommendation, wherein the electronic treatment plan is generated by the trainee and entered by the trainee into the VROC computer system via the user interface or is displayed to the trainee on a display device of the user interface and modified by the trainee via the user interface of the VROC computer system, and
(d) in a computing device of the VROC computer system, computing one or more comparison metrics for the electronic treatment plan and providing training feedback to the trainee via the user interface, wherein said one or more comparison metrics are indicative of whether the electronic treatment plan contains one or more errors, and wherein the feedback includes an indication of whether the electronic treatment plan contains said one or more errors.

2. The method of claim 1, wherein the electronic treatment plan comprises one or more contours on a CT dataset in the electronic medical record.

3. The method of claim 1, further comprising:
(e) with a computing device of the VROC computer system, generating an electronic simulated treatment record for the virtual patient based upon the electronic treatment plan,
(f) with a computing device of the VROC computer system, causing the electronic treatment record to be displayed to the trainee on a display of the user interface for treatment verification.

4. The method of claim 3, wherein the simulated treatment record is simulated to contain one or more patient treatment errors, the method further comprising:
with a computing device of the VROC computer system, causing the electronic simulated treatment record to be displayed to a trainee on a display of the user interface to allow the trainee to identify via the user interface if a treatment error has occurred.

5. The method of claim 4, wherein the treatment errors are selected from the group consisting of a dose error, an error in patient setup during treatment, an error in the treatment time, a technician deviation from the treatment plan, and a combination thereof.

6. The method of claim 1, wherein the electronic simulated treatment record comprises the treatment and daily dose, and an image file selected from the group consisting of a portal image, a kilovoltage X-ray (KV) image, a computed tomography (CT) image, and a combination thereof.

7. The method of claim 1, wherein the comparison metrics comprise a metric selected from the group consisting of a contour metric, a dosimetry metric, a reporting error metric, and a combination thereof.

8. The method of claim 1, wherein the comparison metrics comprise a contour metric selected from the group consisting of a conformity index, a similarity coefficient, a volume metric, and combinations thereof.

9. The method of claim 1, wherein the comparison metrics comprise a dosimetry metric selected from the group consisting of a dose-volume histogram, an equivalent uniform dose, a normal tissue complication probability, a tumor control probability, and a combination thereof.

10. The method of claim 1, wherein the comparison metrics comprise a reporting error metric selected from the group consisting of a detrimental dose, a severity score, and a combination thereof.

11. The method of claim 1, wherein the comparison metrics comprise a normal tissue complication probability, an equivalent uniform dose for a target tissue, an equivalent uniform dose for a normal tissue, a tumor control probability for a target tissue, a percentage of target coverage, a conformity index, a detrimental dose, and a severity score.

12. A virtual radiation oncology clinic (VROC) computer system for radiation oncology training that simulates an entire course of radiation therapy including an evaluation of a virtual patient by a trainee, an identification by the trainee of all therapeutic target and non-target regions of the virtual patient, a recommendation by the trainee of radiation doses to structures of the virtual patient in one or more treatment fractions in one or more treatment fractions, delivery of the recommended radiation doses in one or more treatment fractions to the structures of the virtual patient in accordance with the recommendation and a follow up by the trainee with the virtual patient after delivery of all treatment fractions, the VROC computer system comprising:
 a computing device of the VROC computer system configured to execute a medical record module comprising electronic medical records of a virtual patient,
 a computing device of the VROC computer system configured to execute a treatment simulation module that generates an electronic simulated treatment record for the virtual patient from an electronic treatment plan and the electronic medical records, the electronic treatment plan including the identification by the trainee of all therapeutic target and non-target regions of the virtual patient, the recommendation by the trainee of radiation doses to structures of the virtual patient in one or more treatment fractions, and delivery of the recommended radiation doses in one or more treatment fractions to the structures of the virtual patient in accordance with the recommendation, and
 a computing device of the VROC computer system configured to execute a metrics module that computes one or more comparison metrics from at least one of the electronic treatment plan and the electronic simulated treatment record and causes training feedback to be provided to the trainee via the user interface, wherein said one or more comparison metrics are indicative of whether at least one of the electronic treatment plan and the electronic simulated treatment record contains one or more errors, and wherein the feedback includes an indication of whether at least one of the electronic treatment plan and the electronic simulated treatment record contains said one or more errors.

13. The system of claim 12, further comprising:
 a patient management computer system having a user interface that allows the trainee to view and work with the electronic medical records.

14. The system of claim 12, further comprising:
 a treatment management computer system having a user interface that allows the trainee to view and work with the electronic treatment plan and the electronic simulated treatment record.

15. The system of claim 14, wherein the VROC computer system generates one or more files in digital imaging and communications in medicine (DICOM) format to be used by the treatment management computer system.

16. The system of claim 12, wherein the electronic treatment plan comprises one or more contours on a CT dataset in the electronic medical records.

17. The system of claim 12, wherein the electronic simulated treatment record comprises the treatment and daily dose, and an image file selected from the group consisting of a portal image, a kilovoltage X-ray (KV) image, a computed tomography (CT) image, and a combination thereof.

18. The system of claim 12, wherein the electronic simulated treatment record comprises one or more patient treatment errors selected from the group consisting of a dose error, an error in patient setup during treatment, an error in the treatment time, a technician deviation from the treatment plan, and a combination thereof.

19. A non-transitory computer readable storage medium comprising instructions for execution by one or more computing devices of a virtual radiation oncology clinic (VROC) computer system for radiation oncology training that simulates an entire course of radiation therapy including an evaluation of a virtual patient by a trainee, an identification by the trainee of all therapeutic target and non-target regions of the virtual patient, a recommendation the trainee of radiation doses to structures of the virtual patient in one or more treatment fractions in one or more treatment fractions, delivery of the recommended radiation doses in one or more treatment fractions to the structures of the virtual patient in accordance with the recommendation, and a follow up by the trainee with the virtual patient after delivery of all treatment fractions, the instructions comprising:
 (a) an instruction set for simulating an electronic treatment record for a virtual patient from an electronic treatment plan and an electronic medical record, the electronic treatment plan virtual patient, the recommendation by the trainee of radiation doses to structures of the virtual patient in one or more treatment fractions, and delivery of the recommended radiation doses in one or more treatment fractions to the structures of the virtual patient in accordance with the recommendation,
 (b) an instruction set for computing one or more comparison metrics for at least one of the electronic simulated treatment record and the electronic treatment plan, and
 (c) an instruction set that causes training feedback to be provided to the trainee via a user interface of the VCOR computer system, wherein said one or more comparison metrics are indicative of whether at least one of the electronic treatment plan and the electronic simulated treatment record contains one or more errors, and wherein the feedback includes an indication of whether the electronic treatment plan or the electronic simulated treatment record contains said one or more errors.

20. The storage medium of claim 19, further comprising an instruction set for causing the VROC computer system to read the electronic medical record for the virtual patient from an electronic medical records database used in a patient management system.

* * * * *